(12) United States Patent
Speake

(10) Patent No.: US 9,420,793 B2
(45) Date of Patent: Aug. 23, 2016

(54) ANTIPARASITIC COMPOUNDS

(71) Applicant: Avista Pharma Solutions, Durham, NC (US)

(72) Inventor: Jason D. Speake, Winston-Salem, NC (US)

(73) Assignee: Avista Pharma Solutions, Durham, NC (US)

( * ) Notice: Subject to any disclaimer, the term of this patent is extended or adjusted under 35 U.S.C. 154(b) by 0 days.

(21) Appl. No.: 14/995,547

(22) Filed: Jan. 14, 2016

(65) Prior Publication Data

US 2016/0205936 A1    Jul. 21, 2016

Related U.S. Application Data

(60) Provisional application No. 62/104,364, filed on Jan. 16, 2015.

(51) Int. Cl.
*C07D 491/107*    (2006.01)
*A01N 43/90*    (2006.01)

(52) U.S. Cl.
CPC ........... *A01N 43/90* (2013.01); *C07D 491/107* (2013.01)

(58) Field of Classification Search
USPC ....................................... 548/206
See application file for complete search history.

(56) References Cited

U.S. PATENT DOCUMENTS

| 2012/0232026 A1 | 9/2012 | Curtis et al. |
| 2014/0378415 A1 | 12/2014 | Cassayre et al. |

FOREIGN PATENT DOCUMENTS

| WO | 2007/075459 | 12/2006 |
| WO | 2007/105814 | 3/2007 |
| WO | 2008/096746 | 2/2008 |
| WO | 2008/122375 | 3/2008 |
| WO | 2009/035004 | 9/2008 |
| WO | 2009/063910 | 11/2008 |
| WO | 2009/112275 | 3/2009 |
| WO | 2010/025998 | 7/2009 |
| WO | 2010/032437 | 9/2009 |
| WO | 2010/084067 | 1/2010 |
| WO | 2011/104089 | 2/2011 |
| WO | 2012/017359 | 7/2011 |
| WO | 2012/120399 | 2/2012 |
| WO | 2014/001120 | 6/2013 |
| WO | 2014/001121 | 6/2013 |
| WO | 2013/116230 | 8/2013 |
| WO | 2014/039489 | 9/2013 |
| WO | 2014/079935 | 11/2013 |
| WO | 2014/079941 | 11/2013 |
| WO | 2014/039484 | 3/2014 |
| WO | 2014/206911 | 6/2014 |

OTHER PUBLICATIONS

PCT/US16/13358, filed Jan. 14, 2016, International Search Report, mailed Mar. 29, 2016.

*Primary Examiner* — Laura L. Stockton

(74) *Attorney, Agent, or Firm* — Brinks Gilson & Lione

(57) ABSTRACT

The present invention relates to isothiazoline compounds of formula (I). The compounds are useful for combating or controlling invertebrate pests, in particular arthropod pests and nematodes. The invention also relates to a method for controlling invertebrate pests by using these compounds and to veterinary compositions comprising said compounds.

2 Claims, No Drawings

ANTIPARASITIC COMPOUNDS

This application claims the benefit of U.S. Provisional Patent Application No. 62/104,364, filed Jan. 16, 2015, the entire contents of which are hereby incorporated herein by reference.

FIELD OF THE INVENTION

The present invention includes spirocyclic derivatives having parasiticidal activity. The present invention preferably includes spirocyclic azetidenyl-isobenzofuran derivatives having an isothiazoline moiety. The present invention also includes processes of making said spirocyclic derivatives, compositions comprising said spirocyclic derivatives, and methods of use thereof.

BACKGROUND

There is a need for improved antiparasitics, and in particular there is a need for improved insecticides and acaricides, particularly for use in animal health. Furthermore, there is a need for improved topical and oral products with convenient administration. Still further, there is a need for improved compositions which contains one or more active antiparasitics, which can be used to effectively treat against parasites. Such improvements would be particularly useful for the treatment of animals including: birds (e.g., chickens and turkeys), fish, companion animals (e.g., cats, dogs, llamas, and horses), and livestock (e.g., cattle, bison, swine, sheep, deer, elk, and goats).

Currently available insecticidal and acaricidal treatments for animals do not always demonstrate good activity, good speed of action, or a long duration of action. Most treatments contain hazardous chemicals that can have serious consequences, including neurotoxicity and lethality from accidental ingestion. Persons applying these agents are generally advised to limit their exposure. Pet collars and tags have been utilized to overcome some problems, but these are susceptible to chewing, ingestion, and subsequent toxicological effects to the animal. Thus, current treatments achieve varying degrees of success, which depend partly on toxicity, method of administration, and efficacy. Additionally, some currently available agents are becoming ineffective due to parasitic resistance.

Despite the availability of effective, broad spectrum antiparasitics, there remains a need for safer and more convenient, efficacious, and environmentally friendly products that will overcome the ever-present threat of resistance development. The present invention includes new isothiazoline spiroazetidinyl-isobenzofuran derivatives which demonstrate such properties.

SUMMARY

The present invention includes compounds according to Formula (I), including stereoisomers, and pesticidal, veterinary, or pharmaceutically acceptable salts thereof:

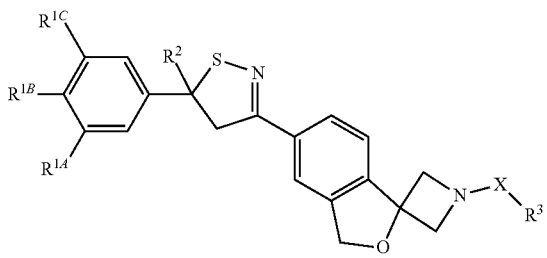

Formula (I)

wherein
each $R^{1A}$, $R^{1B}$, and $R^{1C}$ individually is hydrogen, alkyl, halogen, or haloalkyl;
$R^2$ is haloalkyl;
X is bond, C(O), $SO_2$, or C(O)NH;
$R^3$ is hydrogen, optionally substituted alkyl, optionally substituted haloalkyl, optionally substituted cycloalkyl, optionally substituted heterocyclyl, optionally substituted aryl, and optionally substituted heteroaryl,
or a pesticidal, veterinary, or pharmaceutically acceptable salt thereof.

In one embodiment, the invention includes compounds of Formula (I) wherein:
each $R^{1A}$, $R^{1B}$, and $R^{1C}$ individually is halogen, haloalkyl, or alkyl;
$R^2$ is haloalkyl;
X is a bond, C(O), $SO_2$, or C(O)NH; and
$R^3$ is alkyl, haloalkyl, or aryl.

In one embodiment, the invention includes compounds of Formula (I) wherein:
each $R^{1A}$, $R^{1B}$, and $R^{1C}$ individually is halogen;
$R^2$ is perfluoroalkyl;
X is —C(O)—, —$SO_2$—, or —C(O)NH—; and
$R^3$ is haloalkyl.

In one embodiment, the invention includes compounds of Formula (I) wherein:
each $R^{1A}$ and $R^{1C}$ is a halogen and $R^{1B}$ is a different halogen;
$R^2$ is haloalkyl, preferably —$CF_3$;
X is —C(O)—; and
$R^3$ is haloalkyl, preferably —$CH_2CF_3$.

In one embodiment, the invention includes compounds of Formula (I) wherein:
each $R^{1A}$ and $R^{1C}$ is —Cl and $R^{1B}$ is —F;
$R^2$ is —$CF_3$;
X is —C(O)—; and
$R^3$ is haloalkyl, preferably —$CH_2CF_3$.

In one embodiment, the invention includes compounds of Formula (I) wherein:
each $R^{1A}$ and $R^{1C}$ is —Cl and $R^{1B}$ is —F;
$R^2$ is —$CF_3$;
X is a bond, C(O), $SO_2$, or C(O)NH; and
$R^3$ is hydrogen, optionally substituted alkyl, optionally substituted haloalkyl, optionally substituted cycloalkyl, optionally substituted heterocyclyl, optionally substituted aryl, and optionally substituted heteroaryl.

In one or more embodiments, $R^3$ is alkyl; alkyl substituted with one or more alkoxy, alkylsulfonyl, cyano, or aryl; haloalkyl; cycloalkyl; cycloalkyl substituted with one or more alkyl, alkenyl, haloalkyl, haloalkenyl, alkoxy, or carbonyl; heterocyclyl; aryl; aryl substituted with one or more halogen; or heteroaryl.

One embodiment of the invention includes compositions comprising a compound of formula (I) along with a pesticidally acceptable carrier. The compositions of the invention can also be in a variety of forms which include, but are not limited to, oral formulations, injectable formulations, and topical, dermal, or subdermal formulations. The formulations are intended to be administered to an animal, which includes, but is not limited to, mammals, birds, and fish. Examples of mammals include, but are not limited to, humans, cattle, sheep, goats, llamas, alpacas, pigs, horses, donkeys, dogs, cats, and other livestock or domestic mammals. Examples of birds include turkeys, chickens, ostriches, and other livestock or domestic birds.

The present invention includes compositions comprising a compound of formula (I) suitable for treatment of a locus that may be infected with parasites, such as a plant or animal such as a mammal, or for the prevention of infection or infestation of a locus with parasites.

Another embodiment of the present invention includes combination therapy, whereby one or more compounds of formula (I) can be employed as such or in the form of their preparations or formulations as combinations with one or more other pesticidally active substances, such as, for example, insecticides, attractants, sterilants, nematicides, acaricides, fungicides, herbicides, and with safeners, fertilizers, or growth regulators. The combinations may be part of the same formulation, or may be administered separately or sequentially to the locus.

Another embodiment of the present invention includes a compound of formula (I), or a composition comprising a compound of formula (I), for use in treating or preventing parasitic infection or infestation.

Another embodiment of the present invention includes the use of a compound of formula (I) for the manufacture of a medicament for use in treating or preventing parasitic infection or infestation.

Another embodiment of the present invention includes a method of treating or preventing a parasitic infection comprising the administration of an effective amount of a compound of formula (I), or a composition comprising a compound of formula (I) to a locus.

One embodiment of the present invention is a compound of the present invention selected from:

1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-3,3,3-trifluoro-propan-1-one;

6-[5-(3,5-dichloro-4-fluoro-phenyl)-5-(trifluoromethyl)-4H-isothiazol-3-yl]-N-(2,2,2-trifluoroethyl)spiro[1H-isobenzofuran-3,3'-azetidine]-1'-carboxamide;

6-[5-(3,5-dichloro-4-fluoro-phenyl)-5-(trifluoromethyl)-4H-isothiazol-3-yl]-1'-(4-fluorophenyl)sulfonyl-spiro[1H-isobenzofuran-3,3'-azetidine];

[6-[5-(3,5-dichloro-4-fluoro-phenyl)-5-(trifluoromethyl)-4H-isothiazol-3-yl]spiro[1H-isobenzofuran-3,3'-azetidine]-1'-yl]-phenyl-methanone;

1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-2-methylsulfonyl-ethanone;

6-[5-(3,5-dichloro-4-fluoro-phenyl)-5-(trifluoromethyl)-4H-isothiazol-3-yl]spiro[1H-isobenzofuran-3,3'-azetidine];

1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-3,3-dimethyl-butan-1-one;

1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]butan-1-one;

1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-2-phenyl-ethanone;

1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-4,4,4-trifluoro-butan-1-one;

[6-[5-(3,5-dichloro-4-fluoro-phenyl)-5-(trifluoromethyl)-4H-isothiazol-3-yl]spiro[1H-isobenzofuran-3,3'-azetidine]-1'-yl]-(1-naphthyl)methanone;

[(3Z,4Z)-4-allylidene-3-ethylidene-cyclohexa-1,5-dien-1-yl]-[6-[5-(3,5-dichloro-4-fluoro-phenyl)-5-(trifluoromethyl)-4H-isothiazol-3-yl]spiro[1H-isobenzofuran-3,3'-azetidine]-1'-yl]methanone;

[6-[5-(3,5-dichloro-4-fluoro-phenyl)-5-(trifluoromethyl)-4H-isothiazol-3-yl]spiro[1H-isobenzofuran-3,3'-azetidine]-1'-yl]-(4-morpholinophenyl)methanone;

6-[5-(3,5-dichloro-4-fluoro-phenyl)-5-(trifluoromethyl)-4H-isothiazol-3-yl]-1'-propylsulfonyl-spiro[1H-isobenzofuran-3,3'-azetidine];

6-[5-(3,5-dichloro-4-fluoro-phenyl)-5-(trifluoromethyl)-4H-isothiazol-3-yl]-1'-(3,3,3-trifluoropropylsulfonyl)spiro[1H-isobenzofuran-3,3'-azetidine];

6-[5-(3,5-dichloro-4-fluoro-phenyl)-5-(trifluoromethyl)-4H-isothiazol-3-yl]-N-ethyl-spiro[1H-isobenzofuran-3,3'-azetidine]-1'-carboxamide;

6-[5-(3,5-dichloro-4-fluoro-phenyl)-5-(trifluoromethyl)-4H-isothiazol-3-yl]-N-phenyl-spiro[1H-isobenzofuran-3,3'-azetidine]-1'-carboxamide;

[6-[5-(3,5-dichloro-4-fluoro-phenyl)-5-(trifluoromethyl)-4H-isothiazol-3-yl]spiro[1H-isobenzofuran-3,3'-azetidine]-1'-yl]-[3-(2,2-dichlorovinyl)-2,2-dimethyl-cyclopropyl]methanone;

[6-[5-(3,5-dichloro-4-fluoro-phenyl)-5-(trifluoromethyl)-4H-isothiazol-3-yl]spiro[1H-isobenzofuran-3,3'-azetidine]-1'-yl]-tetrahydropyran-4-yl-methanone;

1'-butyl-6-[5-(3,5-dichloro-4-fluoro-phenyl)-5-(trifluoromethyl)-4H-isothiazol-3-yl]spiro[1H-isobenzofuran-3,3'-azetidine];

6-[5-(3,5-dichloro-4-fluoro-phenyl)-5-(trifluoromethyl)-4H-isothiazol-3-yl]-1'-(3,3-dimethylbutyl)spiro[1H-isobenzofuran-3,3'-azetidine];

1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-2-methoxy-ethanone;

1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-2-isopropoxy-ethanone;

1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-2-ethoxy-ethanone;

1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-2-methyl-propan-1-one;

1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]propan-1-one;

1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]ethanone;

3-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-4-ethoxy-cyclobut-3-ene-1,2-dione;

3-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-3-oxo-propanenitrile;

1-[6-[5-(3,5-dichloro-4-fluoro-phenyl)-5-(trifluoromethyl)-
4H-isothiazol-3-yl]spiro[1H-isobenzofuran-3,3'-azeti-
dine]-1'-yl]-2,2,3,3,3-pentafluoro-propan-1-one;

1-[6-[5-(3,5-dichloro-4-fluoro-phenyl)-5-(trifluoromethyl)-
4H-isothiazol-3-yl]spiro[1H-isobenzofuran-3,3'-azeti-
dine]-1'-yl]-2,2-difluoro-propan-1-one;

[6-[5-(3,5-dichloro-4-fluoro-phenyl)-5-(trifluoromethyl)-
4H-isothiazol-3-yl]spiro[1H-isobenzofuran-3,3'-azeti-
dine]-1'-yl]-[1-(trifluoromethyl)cyclopropyl]methanone;

[6-[5-(3,5-dichloro-4-fluoro-phenyl)-5-(trifluoromethyl)-
4H-isothiazol-3-yl]spiro[1H-isobenzofuran-3,3'-azeti-
dine]-1'-yl]-[1-(trifluoromethyl)cyclobutyl]methanone;

1-[6-[5-(3,5-dichloro-4-fluoro-phenyl)-5-(trifluoromethyl)-
4H-isothiazol-3-yl]spiro[1H-isobenzofuran-3,3'-azeti-
dine]-1'-yl]-3,3,3-trifluoro-2,2-dimethyl-propan-1-one;

1-[6-[5-(3,5-dichloro-4-fluoro-phenyl)-5-(trifluoromethyl)-
4H-isothiazol-3-yl]spiro[1H-isobenzofuran-3,3'-azeti-
dine]-1'-yl]pentan-1-one;

1-[6-[5-(3,5-dichloro-4-fluoro-phenyl)-5-(trifluoromethyl)-
4H-isothiazol-3-yl]spiro[1H-isobenzofuran-3,3'-azeti-
dine]-1'-yl]hexan-1-one;

1-[6-[5-(3,5-dichloro-4-fluoro-phenyl)-5-(trifluoromethyl)-
4H-isothiazol-3-yl]spiro[1H-isobenzofuran-3,3'-azeti-
dine]-1'-yl]heptan-1-one;

1-[6-[5-(3,5-dichloro-4-fluoro-phenyl)-5-(trifluoromethyl)-
4H-isothiazol-3-yl]spiro[1H-isobenzofuran-3,3'-azeti-
dine]-1'-yl]octan-1-one;

1-[6-[5-(3,5-dichloro-4-fluoro-phenyl)-5-(trifluoromethyl)-
4H-isothiazol-3-yl]spiro[1H-isobenzofuran-3,3'-azeti-
dine]-1'-yl]nonan-1-one;

6-[5-(3,5-dichloro-4-fluoro-phenyl)-5-(trifluoromethyl)-
4H-isothiazol-3-yl]-1'-pyrimidin-2-yl-spiro[1H-isoben-
zofuran-3,3'-azetidine]; and 6-[5-(3,5-dichloro-4-fluoro-phenyl)-5-(trifluoromethyl)-
4H-isothiazol-3-yl]-N-methyl-spiro[1H-isobenzofuran-3,
3'-azetidine]-1'-carboxamide, or a pesticidal, veterinary, or pharmaceutically acceptable salt thereof.

One embodiment of the present invention is a composition comprising a compound of the present invention and a pesticidally acceptable carrier. Another embodiment of the present invention is a combination comprising a compound of the present invention and one or more other pesticidally active substances. Another embodiment of the present invention is a method for controlling parasites at a locus comprising applying to the locus an effective amount of a compound of the present invention. Another embodiment of the present invention is a method of treating or preventing parasitic infection or infestation in a subject comprising administering to the subject an effective amount of a compound of the present invention. In one aspect, the parasite is a flea or tick. In one aspect, the parasite is *Ctenocephalides felis, R. sanguineus, D. variablis, A. americanum*, or *I. scapularis*. In one aspect, the parasite is a helminth. In one aspect, the parasite is *Dirofilaria immitis*. Another embodiment is a compound of the present invention for use in treating or preventing parasitic infection or infestation. Another embodiment is a compound of the present invention for use in medicine.

One embodiment of the present invention is a compound 1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-3,3,3-trifluoro-propan-1-one or a pesticidal, veterinary, or pharmaceutically acceptable salt thereof. Another embodiment is a composition comprising 1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-3,3,3-trifluoro-propan-1-one or a pesticidal, veterinary, or pharmaceutically acceptable salt thereof and one or more pesticidal, veterinary, or pharmaceutically acceptable carrier. Another embodiment of the present invention is a combination comprising 1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-3,3,3-trifluoro-propan-1-one or a pesticidal, veterinary, or pharmaceutically acceptable salt thereof and one or more other pesticidally active substances. Another embodiment of the present invention is a method for controlling parasites at a locus comprising applying to the locus an effective amount of 1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-3,3,3-trifluoro-propan-1-one or a pesticidal, veterinary, or pharmaceutically acceptable salt thereof. Another embodiment of the present invention is a method of treating or preventing parasitic infection or infestation in a subject comprising administering to the subject an effective amount of 1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-3,3,3-trifluoro-propan-1-one or a pesticidal, veterinary, or pharmaceutically acceptable salt thereof. In one aspect, the parasite is a flea or tick. In one aspect, the parasite is *Ctenocephalides felis, R. sanguineus, D. variablis, A. americanum*, or *I. scapularis*. In one aspect, the parasite is a helminth. In one aspect, the parasite is *Dirofilaria immitis*. Another embodiment of the present invention is 1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-3,3,3-trifluoro-propan-1-one or a pesticidal, veterinary, or pharmaceutically acceptable salt thereof for use in treating or preventing parasitic infection or infestation. Another embodiment is 1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-3,3,3-trifluoro-propan-1-one or a pesticidal, veterinary, or pharmaceutically acceptable salt thereof for use in medicine.

DETAILED DESCRIPTION

One or more aspects and embodiments may be incorporated in a different embodiment although not specifically described. That is, all aspects and embodiments can be combined in any way or combination.

Definitions

When referring to the compounds disclosed herein, the following terms have the following meanings unless indicated otherwise. The following definitions are meant to clarify, but not limit, the terms defined. If a particular term used herein is not specifically defined, such term should not be considered indefinite. Rather, terms are used within their accepted meanings.

As used herein, the term "alkoxy" refers to the group —OR where R is alkyl. Illustrative alkoxy groups include methoxy, ethoxy, n-propoxy, isopropoxy, n-butoxy, tert-butoxy, sec-butoxy, n-pentoxy, n-hexoxy, and 1,2-dimethylbutoxy.

As used herein, "alkyl" refers to monovalent saturated aliphatic hydrocarbyl groups having from 1 to 20 carbon atoms, preferably 1-8 carbon atoms, preferably 1-6 carbon atoms. The hydrocarbon chain can be either straight-chained or branched. Illustrative alkyl groups include methyl, ethyl, n-propyl, isopropyl, n-butyl, iso-butyl, and tert-butyl. Similarly, an "alkenyl" group refers to an alkyl group having one or more double bonds present in the chain.

As used herein, "cycloalkyl" refers to an unsaturated or partially saturated hydrocarbon ring, containing from 3 to 6 ring atoms. Illustrative cycloalkyl groups include cyclopropyl, cyclobutyl, cyclopentyl, cyclohexyl, as well as partially saturated versions thereof, such as cyclohexenyl, and cyclohexadienyl.

As used herein "halogen" or "halo" refers to a halogen. In some embodiments, the halogen is preferably Br, Cl, or F.

As used herein, "haloalkyl" refers to monovalent saturated aliphatic hydrocarbyl groups having from 1 to 20 carbon atoms, preferably 1-8 carbon atoms, preferably 1-6 carbon atoms, wherein at least one hydrogen atom is substituted by a halogen, including but not limited to perhalo groups where all hydrogen atoms are replaced with halogen atoms. The haloalkyl chain can be either straight-chained or branched. Illustrative alkyl groups include trifluoromethyl, trifluoroethyl, trifluoropropyl, trifluorobutyl, and pentafluoroethyl. Similarly, a "haloalkenyl" group refers to a haloalkyl group having one or more double bonds present in the chain.

As used herein "heterocyclyl" or "heterocycle" refers to an unsaturated or partially saturated ring containing from 3 to 6 ring atoms and from 1 to 4 heteroatoms, which may be the same or different, selected from nitrogen, oxygen and sulfur. Illustrative heterocyclyl groups include oxirane, tetrahydrofuranyl, morpholino, pyrrolidinyl, tetrahydrothiophene, dioxane, and piperidinyl.

As used herein "aryl" refers to an aromatic ring system containing from 5 to 10 ring atoms. Illustrative aryl groups include phenyl and naphthyl.

As used herein "heteroaryl" refers to an heteroaromatic ring system containing from 5 to 10 ring atoms and from 1 to 4 heteroatoms, which may be the same or different, selected from nitrogen, oxygen and sulfur. Illustrative heteroaryl groups include pyridyl (pyridinyl), furan, thiophene, pyrazolyl, tetrazolyl, oxazolyl, thiazolyl, imidazolyl, and pyrimidinyl.

As used herein "optionally substituted" refers to a substitution of a hydrogen atom, which would otherwise be present on the substituent. When discussing ring systems, the optional substitution is typically with 1, 2, or 3 substituents replacing the normally-present hydrogen. When referencing straight and branched moieties, however, the number of substitutions can be more, occurring wherever hydrogen is usually present. The substitutions can be the same or different. Illustrative substitutions include nitro, —NRR", cyano, —NR'COR", alkyl, alkenyl, —C(O), —SO$_2$R'", —NR'SO$_2$R'", —SO$_2$NR'R", —CONR'R", —CONHC$_6$H$_5$, hydroxy, alkoxy, alkylsulfonyl, haloalkyl, haloalkenyl, haloalkoxy, mercapto (—SH), thioalkyl, halogen, cycloalkyl, heterocyclyl, aryl, or heteroaryl, where R' and R" are the same or different and each represents hydrogen or alkyl; or when R' and R" are each attached to a nitrogen atom, they may form a saturated or unsaturated heterocyclic ring containing from 4 to 6 ring atoms, and wherein R" is alkyl or haloalkyl.

As used herein the phrase pesticidal or pesticidally, veterinary or veterinarily, or pharmaceutical or pharmaceutically acceptable salt refers to any salt of a compound disclosed herein which retains its biological properties and which is not toxic or otherwise undesirable for pesticidal, veterinary, or pharmaceutical use. Such salts may be derived from a variety of organic and inorganic counter-ions known in the art. Such salts include: (1) acid addition salts formed with organic or inorganic acids such as hydrochloric, hydrobromic, sulfuric, nitric, phosphoric, sulfamic, acetic, trifluoroacetic, trichloroacetic, propionic, hexanoic, cyclopentylpropionic, glycolic, glutaric, pyruvic, lactic, malonic, succinic, sorbic, ascorbic, malic, maleic, fumaric, tartaric, citric, benzoic, 3-(4-hydroxybenzoyl)benzoic, picric, cinnamic, mandelic, phthalic, lauric, methanesulfonic, ethanesulfonic, 1,2-ethane-disulfonic, 2-hydroxyethanesulfonic, benzenesulfonic, 4-chlorobenzenesulfonic, 2-naphthalenesulfonic, 4-toluenesulfonic, camphoric, camphorsulfonic, 4-methylbicyclo[2.2.2]-oct-2-ene-1-carboxylic, glucoheptonic, 3-phenylpropionic, trimethylacetic, tert-butylacetic, lauryl sulfuric, gluconic, benzoic, glutamic, hydroxynaphthoic, salicylic, stearic, cyclohexylsulfamic, quinic, muconic acid, and like acids.

Salts further include, by way of example only, salts of non-toxic organic or inorganic acids, such as halides, such as, chloride and bromide, sulfate, phosphate, sulfamate, nitrate, acetate, trifluoroacetate, trichloroacetate, propionate, hexanoate, cyclopentylpropionate, glycolate, glutarate, pyruvate, lactate, malonate, succinate, sorbate, ascorbate, malate, maleate, fumarate, tartarate, citrate, benzoate, 3-(4-hydroxybenzoyl)benzoate, picrate, cinnamate, mandelate, phthalate, laurate, methanesulfonate (mesylate), ethanesulfonate, 1,2-ethane-disulfonate, 2-hydroxyethanesulfonate, benzenesulfonate (besylate), 4-chlorobenzenesulfonate, 2-naphthalenesulfonate, 4-toluenesulfonate, camphorate, camphorsulfonate, 4-methylbicyclo[2.2.2]-oct-2-ene-1-carboxylate, glucoheptonate, 3-phenylpropionate, trimethylacetate, tert-butylacetate, lauryl sulfate, gluconate, benzoate, glutamate, hydroxynaphthoate, salicylate, stearate, cyclohexylsulfamate, quinate, muconate, and the like.

In certain cases, the depicted substituents can contribute to optical and/or stereoisomerism. Compounds having the same molecular formula but differing in the nature or sequence of bonding of their atoms or in the arrangement of their atoms in space are termed "isomers." Isomers that differ in the arrangement of their atoms in space are termed "stereoisomers." Stereoisomers that are not mirror images of one another are termed "diastereomers" and those that are non-superimposable mirror images of each other are termed "enantiomers". When a compound has an asymmetric center, for example when it is bonded to four different groups, a pair of enantiomers is possible. An enantiomer can be characterized by the absolute configuration of its asymmetric center and is designated (R) or (S) according to the rules of Cahn and Prelog (Cahn et al., 1966, *Angew. Chem.* 78: 413-447, *Angew. Chem., Int. Ed. Engl.* 5: 385-414 (errata: *Angew. Chem., Int. Ed. Engl.* 5:511); Prelog and Helmchen, 1982, *Angew. Chem.* 94: 614-631, *Angew. Chem. Internat. Ed. Eng.* 21: 567-583; Mata and Lobo, 1993, *Tetrahedron: Asymmetry* 4: 657-668) or can be characterized by the manner in which the molecule rotates the plane of polarized light and is designated dextrorotatory or levorotatory (namely, as (+)- or (−)-isomers, respectively). A chiral compound can exist as either an individual enantiomer or as a mixture thereof. A mixture containing equal proportions of enantiomers is called a "racemic mixture".

In certain embodiments, the compounds disclosed herein can possess one or more asymmetric centers; and such compounds can therefore be produced as the individual (R)- or (S)-enantiomer or as a mixture thereof. Unless indicated otherwise, for example by designation of stereochemistry at any position of a formula, the description or naming of a particular compound in the specification and claims is intended to include both individual enantiomers and mixtures, racemic or otherwise, thereof. Methods for determination of stereochemistry and separation of stereoisomers are well-known in the art. In particular embodiments, stereoisomers of the compounds provided herein are depicted upon treatment with base.

In certain embodiments, the compounds disclosed herein are "stereochemically pure". A stereochemically pure compound has a level of stereochemical purity that would be recognized as "pure" by those of skill in the art. Of course, this level of purity may be less than 100%. In certain embodiments, "stereochemically pure" designates a compound that is substantially free, i.e. at least about 85% or more, of alternate isomers. In particular embodiments, the compound is at least about 85%, about 90%, about 91%, about 92%, about 93%, about 94%, about 95%, about 96%, about 97%, about 98%, about 99%, about 99.5% or about 99.9% free of other isomers.

As used herein, the terms "subject" and "patient" are used interchangeably herein. The terms "subject" and "subjects" refer to a primate such as a monkey such as a cynomolgus monkey, a chimpanzee, and a human or non-primate animal. In one embodiment, the subject is a human. In another embodiment, the subject is a companion animal such as a dog or cat. In a further embodiment the subject is an animal of agricultural importance such as a sheep, cow, horse, goat, fish, pig, or domestic fowl (such as a chicken, turkey, duck, or goose).

In addition, a pharmaceutically acceptable prodrug of the compound represented by the formula (I) is also included in the present invention. The pharmaceutically acceptable prodrug refers to a compound having a group which can be converted into an amino group, a hydroxyl group, a carboxyl group, or the like, by solvolysis or under a physiological condition. Examples of the groups forming the prodrug include those as described in Prog. Med., 5, 2157-2161 (1985) or "Pharmaceutical Research and Development" (Hirokawa Publishing Company, 1990), vol. 7, Drug Design, 163-198. The term prodrug is used throughout the specification to describe any pharmaceutically acceptable form of a compound which, upon administration to a patient, provides the active compound, Pharmaceutically acceptable prodrugs refer to a compound that is metabolized, for example hydrolyzed or oxidized, in the host to form the compound of the present invention. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, dephosphorylated to produce the active compound.

The present invention includes all pharmaceutically acceptable isotopically-labelled compounds of the invention wherein one or more atoms are replaced by atoms having the same atomic number, but an atomic mass or mass number different from the atomic mass or mass number usually found in nature. Examples of isotopes suitable for inclusion in the compounds of the invention include isotopes of hydrogen, such as $^2H$ and $^3H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulfur, such as $^{35}S$. Certain isotopically-labelled compounds of the invention, such as those incorporating a radioactive isotope, may be useful in drug or substrate tissue distribution studies. The radioactive isotopes tritium, i.e. $^3H$, and carbon-14, i.e. $^{14}C$, are particularly useful for this purpose in view of their ease of incorporation and ready means of detection. Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances. Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds of the invention can generally be prepared by conventional techniques known to those skilled in the art or by processes analogous to those described in the accompanying Examples and Preparations using an appropriate isotopically-labeled reagents in place of the non-labeled reagent previously employed.

Compounds

Isoxazoline derivatives have been disclosed in the art as having insecticidal and acaricidal activity. For example, WO2007/105814, WO2008/122375, and WO2009/035004 contain certain alkylene linked amides. WO2010/032437 discloses that the benzyl amide can be moved to the position ortho to the isoxazoline. Further, WO2007/075459 discloses phenyl isoxazolines substituted with 5- to 6-membered heterocycles, and WO2010/084067 and WO2010/025998 disclose phenyl isoxazolines substituted with 10- to 11-membered fused aryl and heteroaryls. Chiral processes for manufacturing isoxazolines have been reported in WO2011/104089 and WO2009/063910. Isoxazoline azetidine derivatives were published in WO2012/017359. Some spiro-azetidine isobenzofuran derivatives for the treatment of diabetes and hyperlipidemia were described in WO2008/096746. In addition, spirocyclic isoxazolines were recently published in WO2012/120399. WO2014/039489 discloses spirocyclic derivatives as antiparisitic agents, including azetidinyl-isobenzofurans, but the citation does not teach or suggest isothiazolines as the heterocyclic moiety. WO2014/079935 discloses a preparation of [4-(isothiazol-3-yl)aryl-thio]acetamide derivatives as insecticides, and WO2014/001121 and WO2014/001120 each disclose the preparation of isothiazole derivatives as insecticidal compounds, but none contain the azetidinyl-isobenzofuran. WO2014/206911 discloses isothiazoline compounds, however, the teaching lacks any azetidenyl-isobenzofuran moiety. WO2014/079941 discloses insecticidal compounds based on N-(arylsulfanylmethyl) carboxamide derivatives. US2014378415 discloses isothiazoline compounds, however, the teaching lacks any azetidenyl-isobenzofuran moiety. WO2009/112275 relates to pesticidal condensed-ring aryl compounds, however, the teaching lacks any azetidenyl-isobenzofuran moiety.

None of the foregoing references teach or suggest non-isoxazoline spirocyclic molecules, or processes of manufacturing such compounds. Nor do the foregoing citations indicate that such compounds would be useful against a spectrum of parasitic species relevant to companion animals, livestock, birds, or fish, and especially against the range of parasitic morphological lifecycle stages.

Synthesis

Generally the compounds of the invention can be prepared, isolated or obtained by any method apparent to those of skill in the art. Exemplary methods of preparation are illustrated by the following schemes.

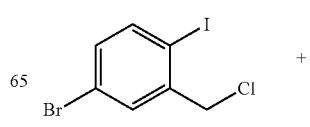

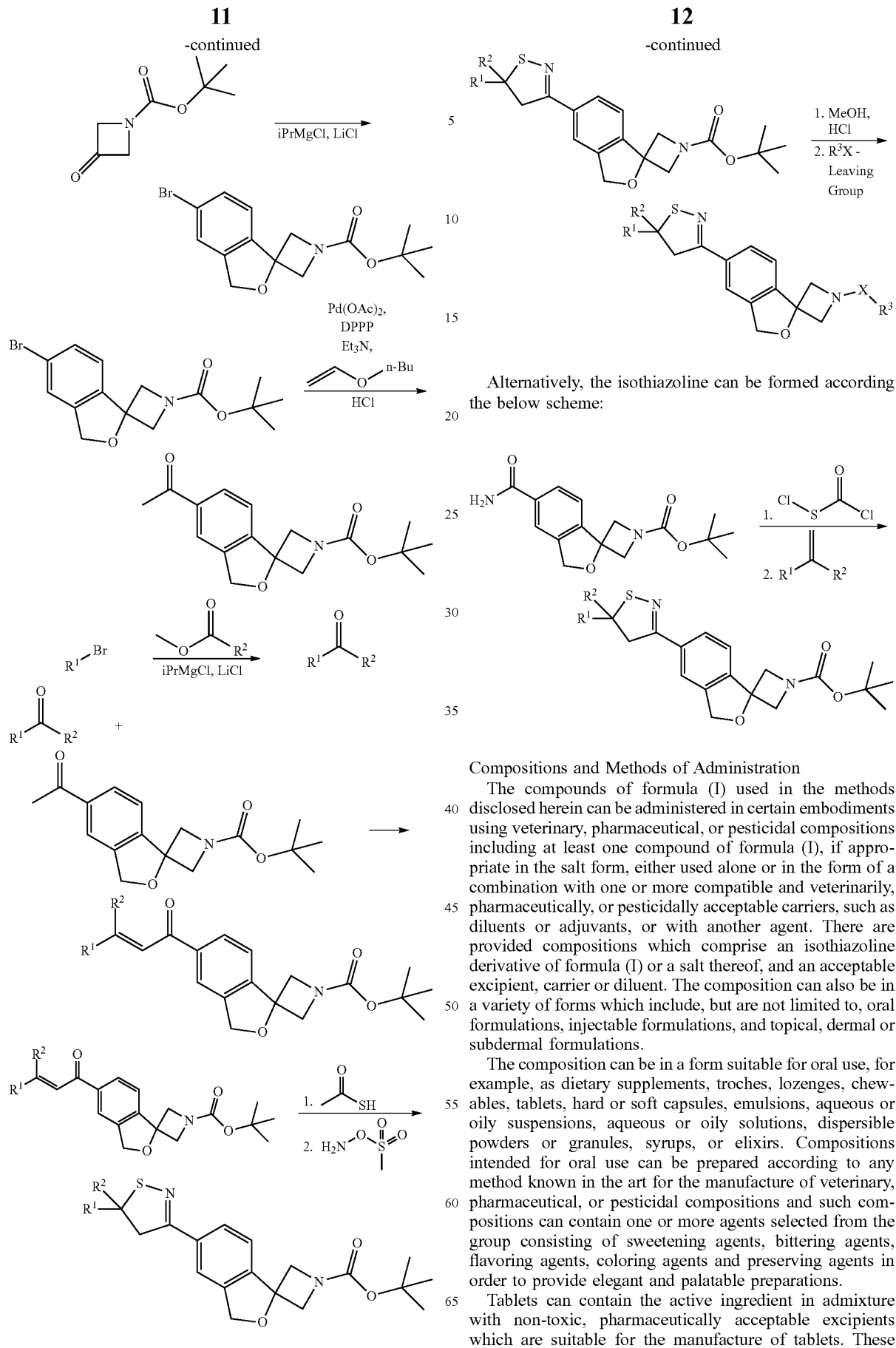

Alternatively, the isothiazoline can be formed according the below scheme:

Compositions and Methods of Administration

The compounds of formula (I) used in the methods disclosed herein can be administered in certain embodiments using veterinary, pharmaceutical, or pesticidal compositions including at least one compound of formula (I), if appropriate in the salt form, either used alone or in the form of a combination with one or more compatible and veterinarily, pharmaceutically, or pesticidally acceptable carriers, such as diluents or adjuvants, or with another agent. There are provided compositions which comprise an isothiazoline derivative of formula (I) or a salt thereof, and an acceptable excipient, carrier or diluent. The composition can also be in a variety of forms which include, but are not limited to, oral formulations, injectable formulations, and topical, dermal or subdermal formulations.

The composition can be in a form suitable for oral use, for example, as dietary supplements, troches, lozenges, chewables, tablets, hard or soft capsules, emulsions, aqueous or oily suspensions, aqueous or oily solutions, dispersible powders or granules, syrups, or elixirs. Compositions intended for oral use can be prepared according to any method known in the art for the manufacture of veterinary, pharmaceutical, or pesticidal compositions and such compositions can contain one or more agents selected from the group consisting of sweetening agents, bittering agents, flavoring agents, coloring agents and preserving agents in order to provide elegant and palatable preparations.

Tablets can contain the active ingredient in admixture with non-toxic, pharmaceutically acceptable excipients which are suitable for the manufacture of tablets. These excipients can be, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period.

Formulations for oral use can be hard gelatin capsules, wherein the active ingredient is mixed with an inert solid diluent, for example, calcium carbonate, calcium phosphate or kaolin. Capsules can also be soft gelatin capsules, wherein the active ingredient is mixed with water or miscible solvents such as propylene glycol, PEGs and ethanol, or an oil medium, for example, peanut oil, liquid paraffin, or olive oil.

The compositions can also be in the form of oil-in-water or water-in-oil emulsions. The oily phase can be a vegetable oil, for example, olive oil or arachis oil, or a mineral oil, for example, liquid paraffin or mixtures of these. Suitable emulsifying agents may be naturally-occurring phosphatides, for example, soy bean, lecithin, and esters or partial esters derived from fatty acids and hexitol anhydrides, for example, sorbitan monoleate, and condensation products of the said partial esters with ethylene oxide, for example, polyoxyethylene sorbitan monooleate. The emulsions can also contain sweetening agents, bittering agents, flavoring agents, and preservatives.

In one embodiment of the formulation, the composition is in the form of a microemulsion. Microemulsions are well suited as the liquid carrier vehicle. Microemulsions are quaternary systems comprising an aqueous phase, an oily phase, a surfactant and a cosurfactant. They are translucent and isotropic liquids. Microemulsions are composed of stable dispersions of microdroplets of the aqueous phase in the oily phase or conversely of microdroplets of the oily phase in the aqueous phase. The size of these microdroplets is less than 200 nm (1000 to 100,000 nm for emulsions). The interfacial film is composed of an alternation of surface-active (SA) and co-surface-active (Co-SA) molecules which, by lowering the interfacial tension, allows the microemulsion to be formed spontaneously. In one embodiment of the oily phase, the oily phase can be formed from mineral or vegetable oils, from unsaturated polyglycosylated glycerides or from triglycerides, or alternatively from mixtures of such compounds. In one embodiment of the oily phase, the oily phase comprises of triglycerides; in another embodiment of the oily phase, the triglycerides are medium-chain triglycerides, for example, $C_8$-$C_{10}$ caprylic/capric triglyceride. In another embodiment, the oily phase will represent a % v/v range selected from the group consisting of about 2 to about 15%; about 7 to about 10%; and about 8 to about 9% v/v of the microemulsion. The aqueous phase includes, for example, water or glycol derivatives, such as propylene glycol, glycol ethers, polyethylene glycols or glycerol. In one embodiment of the glycol derivatives, the glycol is selected from the group consisting of propylene glycol, diethylene glycol monoethyl ether, dipropylene glycol monoethyl ether and mixtures thereof. Generally, the aqueous phase will represent a proportion from about 1 to about 4% v/v in the microemulsion. Surfactants for the microemulsion include diethylene glycol monoethyl ether, dipropylene glycol monomethyl ether, polyglycolyzed $C_8$-$C_{10}$ glycerides or polyglyceryl-6 dioleate. In addition to these surfactants, the cosurfactants include short-chain alcohols, such as ethanol and propanol. Some compounds are common to the three components discussed above, for example, aqueous phase, surfactant and cosurfactant. However, it is well within the skill level of the practitioner to use different compounds for each component of the same formulation. In one embodiment for the amount of surfactant/cosurfactant, the cosurfactant to surfactant ratio will be from about 1/7 to about 1/2.

In another embodiment for the amount of cosurfactant, there will be from about 25 to about 75% v/v of surfactant and from about 10 to about 55% v/v of cosurfactant in the microemulsion.

Oily suspensions can be formulated by suspending the active ingredient in a vegetable oil, for example, atachis oil, olive oil, sesame oil or coconut oil, or in mineral oil such as liquid paraffin. The oily suspensions can contain a thickening agent, for example, beeswax, hard paraffin or cetyl alcohol. Sweetening agents such as sucrose, saccharin or aspartame, bittering agents, and flavoring agents can be added to provide a palatable oral preparation. These compositions can be preserved by the addition of an anti-oxidant such as ascorbic acid, or other known preservatives.

Aqueous suspensions can contain the active material in admixture with excipients suitable for the manufacture of aqueous suspensions. Such excipients are suspending agents, for example, sodium carboxymethylcellulose, methylcellulose, hydroxypropylmethylcellulose, sodium alginate, polvinylpyrrolidone, gum tragacanth and gum acacia; dispersing or wetting agents can be a naturally-occuring phosphatide, for example, lecithin, or condensation products of an alkylene oxide with fatty acids, for example, polyoxyethylene stearate, or condensation products of ethylene oxide with long chain aliphatic alcohols, for example, heptadecaethyleneoxycetanol, or condensation products of ethylene oxide with partial esters derived from fatty acids and a hexitol such as polyoxyethylene sorbitol monooleate, or condensation products of ethylene oxide, with partial esters derived from fatty acids and hexitol anhydrides, for example, polyethylene sorbitan monooleate. The aqueous suspensions can also contain one or more preservatives, for example, ethyl, or n-propyl, p-hydroxybenzoate, one or more coloring agents, one or more flavoring agents, and one or more sweetening agents and/or bittering agents, such as those set forth above.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, bittering, flavoring and coloring agents, can also be present.

Syrups and elixirs can be formulated with sweetening agents, for example, glycerol, propylene glycol, sorbitol or sucrose. Such formulations may also contain a demulcent, a preservative, flavoring agent(s) and coloring agent(s).

The compositions can be in the form of a sterile injectable aqueous or oleagenous suspension. This suspension can be formulated according to the known art using those suitable dispersing or wetting agents and suspending agents which have been mentioned above. The sterile injectable preparation can also be a sterile injectable solution or suspension in a non-toxic parenterally-acceptable diluent or solvent, for example, as a solution in 1,3-butane diol. Among the acceptable vehicles and solvents that can be employed are water, Ringer's solution and isotonic sodium chloride solution. Cosolvents such as ethanol, propylene glycol or polyethylene glycols can also be used. Preservatives, such as phenol or benzyl alcohol, can be used.

In addition, sterile, fixed oils are conventionally employed as a solvent or suspending medium. For this purpose any bland fixed oil can be employed including synthetic mono- or diglycerides. In addition, fatty acids such as oleic acid find use in the preparation of injectables.

Topical, dermal and subdermal formulations can include emulsions, creams, ointments, gels or pastes.

Organic solvents that can be used in the invention include but are not limited to: acetyltributyl citrate, fatty acid esters such as the dimethyl ester, diisobutyl adipate, acetone, acetonitrile, benzyl alcohol, butyl diglycol, dimethylacetamide, dimethylformamide, dipropylene glycol n-butyl ether, ethanol, isopropanol, methanol, ethylene glycol monoethyl ether, ethylene glycol monomethyl ether, monomethylacetamide, dipropylene glycol monomethyl ether, liquid polyoxyethylene glycols, propylene glycol, 2-pyrrolidone (e.g. N-methylpyrrolidone), diethylene glycol monoethyl ether, ethylene glycol and diethyl phthalate, or a mixture of at least two of these solvents.

As vehicle or diluent, compositions of the present invention may include plant oils such as, but not limited to soybean oil, groundnut oil, castor oil, corn oil, cotton oil, olive oil, grape seed oil, sunflower oil, etc.; mineral oils such as, but not limited to, petrolatum, paraffin, silicone, etc.; aliphatic or cyclic hydrocarbons or alternatively, for example, medium-chain (such as $C_8$-$C_{12}$) triglycerides.

Dosage forms can contain from about 0.5 mg to about 5 g of an active agent.

In one embodiment of the invention, the active agent is present in the formulation at a concentration of about 0.05 to 10% weight/volume.

The compounds of formula (I) can be employed as such or in the form of their preparations or formulations as combinations with other pesticidally active substances, such as, for example, insecticides, attractants, sterilants, nematicides, acaricides, fungicides, herbicides, and with safeners, fertilizers and/or growth regulators.

The compounds of formula (I) according to the invention may be combined with one or more agents having the same sphere of activity, for example, to increase activity, or with substances having another sphere of activity, for example, to broaden the range of activity. The compounds of the present invention may also be combined with so-called repellents. By combining the compounds of the formula I with other suitable parasiticides, not only the parasiticidal activity can be enhanced, but the greatest part of those parasites that produce great economic damage will be covered. Moreover, this action will contribute substantially to avoiding the formation of resistance. Preferred groups of combination partners and especially preferred combination partners are named in the following, whereby combinations may contain one or more of these partners in addition to a compound of formula I. Suitable partners may also be afoxolaner, sarolaner, fluralaner, or a combination thereof. Any of the individually listed agents can be used in combination with compounds of formula (I) along with any other one or more listed agents independently.

Suitable partners in the mixture may be biocides, namely insecticides and acaricides with a varying mechanism of activity, for example, chitin synthesis inhibitors, growth regulators, active ingredients which act as juvenile hormones, active ingredients which act as adulticides, broadband insecticides, broadband acaricides and nematicides, and also anthelminthics and insect- and acarid-deterring substances, repellents or detachers. Non-limiting examples of suitable insecticides and acaricides are:

| | |
|---|---|
| 1. | Abamectin |
| 2. | Acephate |
| 3. | Acequinocyl |
| 4. | Acetamiprid |
| 5. | Acetoprole |
| 6. | Acrinathrin |
| 7. | AKD-1022 |
| 8. | Alanycarb |
| 9. | Aldicarb |
| 10. | Aldoxycarb |
| 11. | Allethrin |
| 12. | Alpha-cypermethrin |
| 13. | Alphamethrin |
| 14. | Amidoflumet |
| 15. | Amitraz |
| 16. | Anabasine |
| 17. | Avermectin B1 |
| 18. | Azadirachtin |
| 19. | Azamethiphos |
| 20. | Azinphos-ethyl |
| 21. | Azinphos-methyl |
| 22. | Azocyclotin |
| 23. | *Bacillus subtil*, toxin |
| 24. | *Bacillus thuringiensis* |
| 25. | Benclothiaz |
| 26. | Bendiocarb |
| 27. | Benfuracarb |
| 28. | Bensultap |
| 29. | Benzoximate |
| 30. | Beta-cyfluthrin |
| 31. | Beta-cypermethrin |
| 32. | Bifenazate |
| 33. | Bifenthrin |
| 34. | Bioallethrin |
| 35. | Bioresmethrin |
| 36. | Bistrifluron |
| 37. | BPMC |
| 38. | Brofenprox |
| 39. | Bromophos A |
| 40. | Bromopropylate |
| 41. | Bufencarb |
| 42. | Buprofezin |
| 43. | Butocarboxim |
| 44. | Cadusafos |
| 45. | Carbaryl |
| 46. | Carbofuran |
| 47. | Carbophenothion |
| 48. | Carbosulfan |
| 49. | Cartap |
| 50. | Chloethocarb |
| 51. | Chlorantraniliprole |
| 52. | Chlorethoxyfos |
| 53. | Chlorfenapyr |
| 54. | Chlorfenvinphos |
| 55. | Chlorfluazuron |
| 56. | Chlormephos |
| 57. | Chlorpyrifos |
| 58. | Chlorpyrifos-methyl |
| 59. | Chromafenozide |
| 60. | Cis-Resmethrin |
| 61. | Clofentezin |
| 62. | Clothianidin |
| 63. | Coumaphos |
| 64. | Cyanophos |
| 65. | Cycloprothrin |
| 66. | Cyenopyrafen |
| 67. | Cyflumetofen |
| 68. | Cyfluthrin |
| 69. | Cyhalothrin |
| 70. | Cyhexatin |
| 71. | Cymiazole |
| 72. | Cypermethrin |
| 73. | Cyphenothrin |
| 74. | Cyromazine |
| 75. | Deltamethrin |
| 76. | Demeton M |
| 77. | Demeton S |

| | |
|---|---|
| 78. | Demeton-S-methyl |
| 79. | Diafenthiuron |
| 80. | Diazinon |
| 81. | Dichlofenthion |
| 82. | Dichlorvos |
| 83. | Dicofol |
| 84. | Dicrotophos |
| 85. | Dicyclanil |
| 86. | Diethion |
| 87. | Diflovidazin |
| 88. | Diflubenzuron |
| 89. | Dimefluthrin |
| 90. | Dimethoate |
| 91. | Dimethylvinphos |
| 92. | Dinobuton |
| 93. | Dinocap |
| 94. | Dinotefuran |
| 95. | Diofenolan |
| 96. | Dioxathion |
| 97. | Disulfoton |
| 98. | DNOC |
| 99. | Doramectin |
| 100. | DPX-HGW86 |
| 101. | Edifenphos |
| 102. | Emamectin |
| 103. | Empenthrin |
| 104. | Endosulfan |
| 105. | Esfenvalerat |
| 106. | Ethiofencarb |
| 107. | Ethion |
| 108. | Ethiprole |
| 109. | Ethoprophos |
| 110. | Etofenprox |
| 111. | Etoxazole |
| 112. | Etrimphos |
| 113. | Fenamiphos |
| 114. | Fenazaquin |
| 115. | Fenbutatin oxide |
| 116. | Fenitrothion |
| 117. | Fenobucarb |
| 118. | Fenothiocarb |
| 119. | Fenoxycarb |
| 120. | Fenpropathrin |
| 121. | Fenpyroximate |
| 122. | Fenthion |
| 123. | Fenvalerate |
| 124. | Fipronil |
| 125. | Flonicamid |
| 126. | Fluacrypyrim |
| 127. | Fluazinam |
| 128. | Fluazuron |
| 129. | Flubendiamide |
| 130. | Flucycloxuron |
| 131. | Flucythrinate |
| 132. | Flufenerim |
| 133. | Flufenoxuron |
| 134. | Flufenprox |
| 135. | Flumethrin |
| 136. | Fonophos |
| 137. | Formothion |
| 138. | Fosthiazate |
| 139. | Fubfenprox |
| 140. | Furathiocarb |
| 141. | Gamma-cyhalothrin |
| 142. | Halfenprox |
| 143. | Halofenozide |
| 144. | HCH |
| 145. | Heptenophos |
| 146. | Hexaflumuron |
| 147. | Hexythiazox |
| 148. | Hydramethylnon |
| 149. | Hydroprene |
| 150. | Imidacloprid |
| 151. | Imiprothrin |
| 152. | Indoxacarb |
| 153. | insect-active fungi |
| 154. | insect-active nematodes |
| 155. | insect-active viruses |
| 156. | Iprobenfos |
| 157. | Lsofenphos |
| 158. | Isoprocarb |
| 159. | Isoxathion |
| 160. | Ivermectin |
| 161. | Karanjin |
| 162. | Kinoprene |
| 163. | Lamba-Cyhalothrin |
| 164. | Lepimectin |
| 165. | Lufenuron |
| 166. | Malathion |
| 167. | Mecarbam |
| 168. | Mesulfenphos |
| 169. | Metaflumizone |
| 170. | Metaldehyde |
| 171. | Methamidophos |
| 172. | Methidathion |
| 173. | Methiocarb |
| 174. | Methomyl |
| 175. | Methoprene |
| 176. | Methothrin |
| 177. | Methoxyfenozide |
| 178. | Metofluthrin |
| 179. | Metolcarb |
| 180. | Metoxadiazone |
| 181. | Mevinphos |
| 182. | Milbemectin |
| 183. | Milbemycin oxime |
| 184. | Monocrotophos |
| 185. | Moxidectin |
| 186. | Naled |
| 187. | Nicotine |
| 188. | Nitenpyram |
| 189. | Novaluron |
| 190. | Noviflumuron |
| 191. | Omethoate |
| 192. | Oxamyl |
| 193. | Oxydemethon M |
| 194. | Oxydeprofos |
| 195. | Parathion |
| 196. | Parathion-methyl |
| 197. | Permethrin |
| 198. | Phenothrin |
| 199. | Phenthoate |
| 200. | Phorate |
| 201. | Phosalone |
| 202. | Phosmet |
| 203. | Phosphamidon |
| 204. | Phoxim |
| 205. | Pirimicarb |
| 206. | Pirimiphos A |
| 207. | Pirimiphos M |
| 208. | Polynactins |
| 209. | Prallethrin |
| 210. | Profenofos |
| 211. | Profluthrin |
| 212. | Promecarb |
| 213. | Propafos |
| 214. | Propargite |
| 215. | Propoxur |
| 216. | Prothiofos |
| 217. | Prothoate |
| 218. | Protrifenbute |
| 219. | Pymetrozine |
| 220. | Pyrachlofos |
| 221. | Pyrafluprole |
| 222. | Pyresmethrin |
| 223. | Pyrethrin |
| 224. | Pyrethrum |
| 225. | Pyridaben |
| 226. | Pyridalyl |
| 227. | Pyridaphenthion |
| 228. | Pyrifluquinazon |
| 229. | Pyrimidifen |
| 230. | Pyriprole |
| 231. | Pyriproxyfen |
| 232. | Quinalphos |
| 233. | Resmethrin |
| 234. | Rotenone |
| 235. | RU 15525 |

| | |
|---|---|
| 236. | Sabadilla |
| 237. | Salithion |
| 238. | Selamectin |
| 239. | Silafluofen |
| 240. | Spinetoram |
| 241. | Spinosad |
| 242. | Spirodiclofen |
| 243. | Spiromesifen |
| 244. | Spirotetramat |
| 245. | Sulcofuron sodium |
| 246. | Sulfluramid |
| 247. | Sulfotep |
| 248. | Sulfur |
| 249. | Sulprofos |
| 250. | Tau-fluvalinate |
| 251. | Tebufenozide |
| 252. | Tebufenpyrad |
| 253. | Tebupirimfos |
| 254. | Teflubenzuron |
| 255. | Tefluthrin |
| 256. | Temephos |
| 257. | Terbufos |
| 258. | Tetrachlorvinphos |
| 259. | Tetradifon |
| 260. | Tetramethrin |
| 261. | Thiacloprid |
| 262. | Thiamethoxam |
| 263. | Thiocyclam |
| 264. | Thiodicarb |
| 265. | Thiofanox |
| 266. | Thionazin |
| 267. | Thiosultap |
| 268. | Thuringiensin |
| 269. | Tolfenpyrad |
| 270. | Tralomethrin |
| 271. | Transfluthrin |
| 272. | Triarathene |
| 273. | Triazamate |
| 274. | Triazophos |
| 275. | Trichlorfon |
| 276. | Triflumuron |
| 277. | Trimethacarb |
| 278. | Vamidothion |
| 279. | Vaniliprole |
| 280. | XMC (3,5,-Xylylmethylcarbamate) |
| 281. | Xylylcarb |
| 282. | Zeta-cypermethrin |
| 283. | Zetamethrin |
| 284. | ZXI 8901 |
| 285. | Demiditraz |
| 286. | Afoxolaner |
| 287. | Sarolaner |
| 288. | Fluralaner |

Non-limitative examples of suitable anthelmintics, a few representatives have anthelmintic activity in addition to the insecticidal and acaricidal activity include:

| | | | | | |
|---|---|---|---|---|---|
| (A1) | Abamectin | (A2) | Albendazole | (A3) | Cambendazole |
| (A4) | Closantel | (A5) | Diethylcarbamazine | (A6) | Doramectin |
| (A7) | Emodepside | (A8) | Eprinomectin | (A9) | Febantel |
| (A10) | Fendendazole | (A11) | Flubendazole | (A12) | Ivermectin |
| (A13) | Levamisol | (A14) | Mebendazole | (A15) | Milbemectin |
| (A16) | Milbemycin Oxime | (A17) | Morantel | (A18) | Moxidectin |
| (A19) | Nitroscanate | (A20) | Omphalotin | (A21) | Oxantel |
| (A22) | Oxfendazole | (A23) | Oxibendazole | (A24) | Phenothiazine |
| (A25) | Piperazine | (A26) | PNU-97333 | (A27) | PNU-141962 |
| (A28) | Praziquantel | (A29) | Pyrantel | (A30) | Thiabendazole |
| (A31) | Triclabendazole amino acetonitrile derivatives named in WO2005044784 | | | | |

Non-limitative examples of suitable repellents and detachers include:

(R1) DEET (N, N-diethyl-m-toluamide)

(R2) KBR 3023, picaridin, N-butyl-2-oxycarbonyl-(2-hydroxy)-piperidine (R3) Cymiazole, N,-2,3-dihydro-3-methyl-1,3-thiazol-2-ylidene-2,4-xylidene The above-specified combination partners are best known to specialists in this field. Most are described in various editions of the Pesticide Manual, The British Crop Protection Council, London, in various editions of the Compendium of Veterinary Products, North American Compendiums, Inc., in various editions of the Compendium of Pesticide Common Names and in various editions of the Merck Veterinary Manual and The Merck Index, Merck & Co., Inc., Rahway, N.J., USA.

The pharmaceutical preparation comprising the isothiazoline derivatives, for delivery to a human or other mammal, is preferably in unit dosage form, in which the preparation is subdivided into unit doses containing an appropriate quantity of the active component. The unit dosage form can be a packaged preparation containing discrete quantities of the preparation, such as packaged tablets, capsules, and powders in vials or ampoules. Also, the unit dosage form can be a capsule, tablet or lozenge itself, or it can be an appropriate number of any of these in packaged form.

The quantity of active component in a unit dose preparation can be varied or adjusted from about 0.1 mg to about 1000 mg, according to the particular application and the potency of the active component. The composition can, if desired, also contain other compatible therapeutic agents.

In therapeutic use for the treatment or prevention of a parasitic infection in a human or other mammal, the compounds utilized in the method of treatment are administered at an initial dosage of about 0.1 mg/kg to about 100 mg/kg per interval. Preferred intervals may be daily, weekly, monthly, quarterly, semi-annually, or annually. The dosages can be varied depending on the requirements of the patient, for example, the size of the human or mammal being treated, the severity of the condition being treated, the route of administration, and the potency of the compound(s) being used. Determination of the proper dosage and route of administration for a particular situation is within the skill of the practitioner. Generally, the treatment will be initiated with smaller dosages which are less than the optimum dose of the compound, which can be increased in small increments until the optimum effect under the particular circumstances of the infection is reached. For convenience, the total daily dosage can be divided and administered in portions during the day if desired.

The compounds of the present invention, stereoisomers thereof, and compositions comprising a therapeutically effective amount of a Formula (I) compound, stereoisomer thereof, and veterinarily acceptable salt thereof, and a veterinarily acceptable excipient, diluent, or carrier are useful as ectoparasiticides for the control and treatment of infections or infestations manifested by said ectoparasite in an animal. The compounds of the present invention are illustrated herein to have utility as an ectoparasiticide, in particular, as an acaricide and insecticide. They may, in particular, be used in the fields of veterinary medicine, livestock husbandry and the maintenance of public health: against acarids, insects, and copepods which are parasitic upon vertebrates, particularly warm-blooded vertebrates, including companion animals, livestock, and fowl and cold-blooded vertebrates like fish. Non-limiting examples of ectoparasites include: ticks (e.g., *Ixodes* spp., (e.g., *I. ricinus*, *I. hexagonus*), *Rhipicephalus* spp. (e.g., *R. sanguineus*), *Boophilus* spp., *Amblyomma* spp. (e.g., *A. americanum*, *A.* maculatum, A. triste, A. parvum, A. cajennense, A. ovale, A. oblongoguttatum, A. aureolatum, A. cajennense), Hyalomma spp., Haemaphysalis spp., Dermacentor spp. (e.g., D. variabilis, D. andersoni, D. marginatus), Ornithodorus spp., and the like); mites (e.g., Dermanyssus spp., Sarcoptes spp. (e.g., S. scabiei), Psoroptes spp. (e.g., P. bovis), Otodectes spp., Chorioptes spp., Demodex spp., (e.g., D. folliculorum, D. canis, and D. brevis) and the like); chewing and sucking lice (e.g., Damalinia spp., Linognathus spp., Cheyletiella spp., Haematopinus spp., Solenoptes spp., Trichodectes spp., Felicola spp., and the like); fleas (e.g., Siphonaptera spp., Ctenocephalides spp., and the like); biting flies, midges, and mosquitos (e.g., Tabanidae spp., Haematobia spp., Musca spp., Stomoxys spp., Dematobia spp., Cochliomyia spp., Simuliidae spp., Ceratopogonidae spp., Psychodidae spp., Aedes spp., Culex spp., Anopheles spp., Lucilia spp., Phlebotomus spp., Lutzomyia spp., and the like); bed bugs (e.g., insects within the genus Cimex and family Cimicidae); and grubs (e.g., Hypoderma bovis, H. lineatum); and copepods (e.g., sea lice within the Order Siphonostomatoida, including genera Lepeophtheirus and Caligus).

The compound of the present invention can also be used for the treatment of endoparasites, for example, helminths (e.g., trematodes, cestodes, and nematodes) including heartworm, roundworm, hookworm, whipworm, fluke, and tapeworm. The gastrointestinal roundworms include, for example, Ostertagia ostertagi (including inhibited larvae), O. lyrata, Haemonchus placei, H. similis, H. contortus, Toxocara canis, T. leonina, T. cati, Trichostrongylus axei, T. colubriformis, T. longispicularis, Cooperia oncophora, C. pectinata, C. punctata, C. surnabada (syn. mcmasteri), C. spatula, Ascaris suum, Hyostrongylus rubidus, Bunostomum phlebotomum, Capillaria bovis, B. trigonocephalum, Strongyloides papillosus, S. ransomi, Oesophagostomum radiatum, O. dentatum, O. columbianum, O. quadrispinulatum, Trichuris spp., and the like. Other parasites include: hookworms (e.g., Ancylostoma caninum, A. tubaeforme, A. braziliense, Uncinaria stenocephala); lungworms (e.g., Dictyocaulus viviparus and Metastrongylus spp); eyeworms (e.g., Thelazia spp.); parasitic stage grubs (e.g., Hypoderma bovis, H. lineatum, Dermatobia hominis); kidneyworms (e.g., Stephanurus dentatus); screw worm (e.g., Cochliomyia hominivorax (larvae); filarial nematodes of the superfamily Filarioidea and the Onchocercidae Family. Non-limiting examples of filarial nematodes within the Onchocercidae Family include the genus Brugia spp. (i.e., B. malayi, B. pahangi, B. timori, and the like), Wuchereria spp. (i.e., W. bancrofti, and the like), Dirofilaria spp. (D. immitis, D. repens, D. ursi, D. tenuis, D. spectans, D. lutrae, and the like), Dipetalonema spp. (i.e., D reconditum, D. repens, and the like), Onchocerca spp. (i.e., O. gibsoni, O. gutturosa, O. volvulus, and the like), Elaeophora spp. (E. bohmi, E. elaphi, E. poeli, E. sagitta, E. schneideri, and the like), Mansonella spp. (i.e., M. ozzardi, M. perstans, and the like), and Loa spp. (i.e., L. loa).

Preferably, the compounds of the present invention are used to treat parasitic infection or infestation, preferably wherein the parasite is a flea or tick. In particularly preferred embodiments, the parasite is C. felis, R. sanguineis, A. americanum, I. scapularis, A. maculate, D. variabilis, or I. ricinus.

In another aspect of the invention, the compound of the present invention is useful for treating endoparasiticidal infection from helminths/filarial nematodes within the genus Dirofilaria (i.e., D. immitis, D. repens, D. ursi, D. tenuis, and the like).

The compounds of the present invention, stereoisomers thereof, and veterinarily or pharmaceutically acceptable salts thereof, and compositions comprising compounds of the present invention in conjunction with at least one other veterinary agent are of particular value in the control of ectoparasites, endoparasites, and insects which are injurious to, or spread or act as vectors of diseases in companion animals, livestock, birds, and fish.

Any of the compounds of the present invention, or a suitable combination of a compound of the present invention and optionally, with at least one additional veterinary agent may be administered directly to the animal and/or indirectly by applying it to the local environment in which the animal dwells (such as bedding, enclosures, and the like). Direct administration includes contacting the skin, fur, or feathers of a subject animal with the compound(s), or by feeding or injecting the compounds into the animal.

The Formula (I) compound, stereoisomer thereof, and veterinarily acceptable salt thereof, and combinations with at least one additional veterinary agent, as described herein, are believed to be of value for the treatment and control of the various lifecycle stages of insects and parasites including egg, nymph, larvae, juvenile and adult stages.

The present invention also relates to a method of administering a compound of the present invention alone or in combination with at least one additional veterinary agent, and optionally a veterinarily acceptable excipient, diluent, or carrier, to animals in good health comprising the application to said animal to reduce or eliminate the potential for human parasitic infection or infestation from parasites carried by the animal and to improve the environment in which the animals inhabit.

The present invention explicitly encompasses those compounds presented in Table 1. A composition comprising a therapeutically acceptable amount of any of these compounds is also within the scope of the invention. The composition can further comprise a veterinarily acceptable excipient, diluent, carrier, or mixture thereof. Such a composition can be administered to an animal in need thereof to treat and/or prevent a parasitic infection or infestation. The composition can further comprise an additional veterinary agent, as described herein.

TABLE 1

| Ref. No. | Compound Name |
|---|---|
| 1 | 1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-3,3,3-trifluoro-propan-1-one |
| 2 | 6-[5-(3,5-dichloro-4-fluoro-phenyl)-5-(trifluoromethyl)-4H-isothiazol-3-yl]-N-(2,2,2-trifluoroethyl)spiro[1H-isobenzofuran-3,3'-azetidine]-1'-carboxamide |
| 3 | 6-[5-(3,5-dichloro-4-fluoro-phenyl)-5-(trifluoromethyl)-4H-isothiazol-3-yl]-1'-(4-fluorophenyl)sulfonyl-spiro[1H-isobenzofuran-3,3'-azetidine] |
| 4 | [6-[5-(3,5-dichloro-4-fluoro-phenyl)-5-(trifluoromethyl)-4H-isothiazol-3-yl]spiro[1H-isobenzofuran-3,3'-azetidine]-1'-yl]-phenyl-methanone |

TABLE 1-continued

| Ref. No. | Compound Name |
|---|---|
| 5 | 1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-2-methylsulfonyl-ethanone |
| 6 | 6-[5-(3,5-dichloro-4-fluoro-phenyl)-5-(trifluoromethyl)-4H-isothiazol-3-yl]spiro[1H-isobenzofuran-3,3'-azetidine] |
| 7 | 1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-3,3-dimethyl-butan-1-one |
| 8 | 1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]butan-1-one |
| 9 | 1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-2-phenyl-ethanone |
| 10 | 1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-4,4,4-trifluoro-butan-1-one |
| 11 | [6-[5-(3,5-dichloro-4-fluoro-phenyl)-5-(trifluoromethyl)-4H-isothiazol-3-yl]spiro[1H-isobenzofuran-3,3'-azetidine]-1'-yl]-(1-naphthyl)methanone |
| 12 | [(3Z,4Z)-4-allylidene-3-ethylidene-cyclohexa-1,5-dien-1-yl]-[6-[5-(3,5-dichloro-4-fluoro-phenyl)-5-(trifluoromethyl)-4H-isothiazol-3-yl]spiro[1H-isobenzofuran-3,3'-azetidine]-1'-yl]methanone |
| 13 | [6-[5-(3,5-dichloro-4-fluoro-phenyl)-5-(trifluoromethyl)-4H-isothiazol-3-yl]spiro[1H-isobenzofuran-3,3'-azetidine]-1'-yl]-(4-morpholinophenyl)methanone |
| 14 | 6-[5-(3,5-dichloro-4-fluoro-phenyl)-5-(trifluoromethyl)-4H-isothiazol-3-yl]-1'-propylsulfonyl-spiro[1H-isobenzofuran-3,3'-azetidine] |
| 15 | 6-[5-(3,5-dichloro-4-fluoro-phenyl)-5-(trifluoromethyl)-4H-isothiazol-3-yl]-1'-(3,3,3-trifluoropropylsulfonyl)spiro[1H-isobenzofuran-3,3'-azetidine] |
| 16 | 6-[5-(3,5-dichloro-4-fluoro-phenyl)-5-(trifluoromethyl)-4H-isothiazol-3-yl]-N-ethyl-spiro[1H-isobenzofuran-3,3'-azetidine]-1'-carboxamide |
| 17 | 6-[5-(3,5-dichloro-4-fluoro-phenyl)-5-(trifluoromethyl)-4H-isothiazol-3-yl]-N-phenyl-spiro[1H-isobenzofuran-3,3'-azetidine]-1'-carboxamide |
| 18 | [6-[5-(3,5-dichloro-4-fluoro-phenyl)-5-(trifluoromethyl)-4H-isothiazol-3-yl]spiro[1H-isobenzofuran-3,3'-azetidine]-1'-yl]-[3-(2,2-dichlorovinyl)-2,2-dimethyl-cyclopropyl]methanone |
| 19 | [6-[5-(3,5-dichloro-4-fluoro-phenyl)-5-(trifluoromethyl)-4H-isothiazol-3-yl]spiro[1H-isobenzofuran-3,3'-azetidine]-1'-yl]-tetrahydropyran-4-yl-methanone |
| 20 | 1'-butyl-6-[5-(3,5-dichloro-4-fluoro-phenyl)-5-(trifluoromethyl)-4H-isothiazol-3-yl]spiro[1H-isobenzofuran-3,3'-azetidine] |
| 21 | 6-[5-(3,5-dichloro-4-fluoro-phenyl)-5-(trifluoromethyl)-4H-isothiazol-3-yl]-1'-(3,3-dimethylbutyl)spiro[1H-isobenzofuran-3,3'-azetidine] |
| 22 | 1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-2-methoxy-ethanone |
| 23 | 1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-2-isopropoxy-ethanone |
| 24 | 1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-2-ethoxy-ethanone |
| 25 | 1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-2-methyl-propan-1-one |
| 26 | 1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]propan-1-one |
| 27 | 1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]ethanone |
| 28 | 3-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-4-ethoxy-cyclobut-3-ene-1,2-dione |
| 29 | 3-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-3-oxo-propanenitrile |
| 30 | 1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-2,2,3,3,3-pentafluoro-propan-1-one |
| 31 | 1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-2,2-difluoro-propan-1-one |
| 32 | [6-[5-(3,5-dichloro-4-fluoro-phenyl)-5-(trifluoromethyl)-4H-isothiazol-3-yl]spiro[1H-isobenzofuran-3,3'-azetidine]-1'-yl]-[1-(trifluoromethyl)cyclopropyl]methanone |
| 33 | [6-[5-(3,5-dichloro-4-fluoro-phenyl)-5-(trifluoromethyl)-4H-isothiazol-3-yl]spiro[1H-isobenzofuran-3,3'-azetidine]-1'-yl]-[1-(trifluoromethyl)cyclobutyl]methanone |
| 34 | 1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-3,3,3-trifluoro-2,2-dimethyl-propan-1-one |
| 35 | 1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]pentan-1-one |
| 36 | 1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]hexan-1-one |
| 37 | 1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]heptan-1-one |
| 38 | 1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]octan-1-one |
| 39 | 1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]nonan-1-one |
| 40 | 6-[5-(3,5-dichloro-4-fluoro-phenyl)-5-(trifluoromethyl)-4H-isothiazol-3-yl]-1'-pyrimidin-2-yl-spiro[1H-isobenzofuran-3,3'-azetidine] |
| 41 | 6-[5-(3,5-dichloro-4-fluoro-phenyl)-5-(trifluoromethyl)-4H-isothiazol-3-yl]-N-methyl-spiro[1H-isobenzofuran-3,3'-azetidine]-1'-carboxamide |

Experimental Procedures:

Synthesis

The following Examples illustrate the synthesis of representative compounds of formula (I). These examples are not intended, nor are they to be construed, as limiting the scope of the embodiments disclosed herein. It will be clear that various embodiments may be practiced otherwise than as particularly described herein. Numerous modifications and variations are possible in view of the teachings herein and, therefore, are within the scope.

Liquid chromatography—mass spectrometry (LCMS) experiments to determine retention times and associated mass ions were performed using one or more of the following Methods A, B, and C:

Method A: Waters BEH C18, 3.0×30 mm, 1.7 μm, was used at a temperature of 50° C. and at a flow rate of 1.5 mL/min, 2 μL injection, mobile phase: (A) water with 0.1% formic acid and 1% acetonitrile, mobile phase (B) MeOH with 0.1% formic acid; retention time given in minutes.

Method A details: (I) ran on a Binary Pump G1312B with UV/Vis diode array detector G1315C and Agilent 6130 mass spectrometer in positive and negative ion electrospray mode with UV PDA detection with a gradient of 15-95% (B) in a 2.2 min linear gradient (II) hold for 0.8 min at 95% (B) (III) decrease from 95-15% (B) in a 0.1 min linear gradient (IV) hold for 0.29 min at 15% (B);

Method B: An Agilent Zorbax Bonus RP, 2.1×50 mm, 3.5 μm, was used at a temperature of 50° C. and at a flow rate of 0.8 mL/min, 2 μL injection, mobile phase: (A) water with 0.1% formic acid and 1% acetonitrile, mobile phase (B) MeOH with 0.1% formic acid; retention time given in minutes.

Method B details: (I) ran on a Binary Pump G1312B with UV/Vis diode array detector G1315C and Agilent 6130 mass spectrometer in positive and negative ion electrospray mode with UV-detection at 220 and 254 nm with a gradient of 5-95% (B) in a 2.5 min linear gradient (II) hold for 0.5 min at 95% (B) (Ill) decrease from 95-5% (B) in a 0.1 min linear gradient (IV) hold for 0.29 min at 5% (B).

Method C: An API 150EX mass spectrometer linked to a Shimadzu LC-10AT LC system with a diode array detector was used. The spectrometer had an electrospray source operating in positive and negative ion mode. LC was carried out using an Agilent ZORBAX XDB 50×2.1 mm C18 column and a 0.5 mL/minute flow rate. Solvent A: 95% water, 5% acetonitrile containing 0.01% formic acid; Solvent B: acetonitrile. The gradient was shown as below. 0-0.5 min: 2% solvent (B); 0.5-2.5 min: 2% solvent B to 95% solvent (B); 2.5-4.0 min: 95% solvent (B); 4.0-4.2 min: 95% solvent (B) to 2% solvent B; 4.2-6.0 min: 2% solvent (B).

EXAMPLES

The following Examples provide a more detailed description of the process conditions for preparing compounds of the present invention. It is to be understood, however, that the invention, as fully described herein and as recited in the claims, is not intended to be limited by the details of the following schemes or modes of preparation.

Example 1

1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-3,3,3-trifluoro-propan-1-one Intermediate 1: tert-butyl 5'-bromo-3'H-spiro[azetidine-3,1'-isobenzofuran]-1-carboxylate

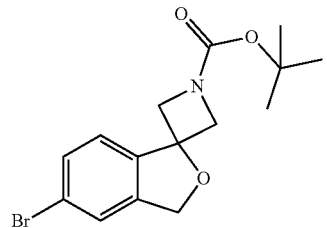 [SMILES: CC(C)(C)OC(=O)N1CC2(C1)OCc1cc(Br)ccc12]

To a solution of 4-bromo-2-(chloromethyl)-1-iodobenzene (2.0 g, 6.04 mmol, 1 eq) in THF (16 mL), isopropylmagnesium chloride lithium chloride complex (5.11 mL, 1.3M in THF, 1.1 eq) was added over about 5 min while the internal temperature didn't exceed −15° C. Reaction is stirred at −15° C. for 30 min. Then a solution of 1-Boc-3-azetidinone (1.24 g, 1.2 eq) in THF (4 mL) was added dropwise; internal temperature at −30° C. The reaction is stirred at room temperature overnight. Reaction was quenched with a solution of citric acid (14 mL of 1M). This was extracted with MTBE and organic layer was washed with aqueous NaHCO$_3$ and brine, dried over MgSO$_4$, filtered and concentrated under reduced pressure. The crude yellow oil is submitted to silica gel column chromatography (0 to 50% ethyl acetate in heptane). 1.6 g of tert-butyl 5'-bromo-3'H-spiro[azetidine-3,1'-isobenzofuran]-1-carboxylate was obtained.

$^1$H NMR (400 MHz, CDCl$_3$) δ ppm 1.47-1.50 (m, 9H) 4.11 (d, J=9.42 Hz, 2H) 4.31 (d, J=9.42 Hz, 2H) 5.09 (s, 2H) 7.32-7.38 (m, 2H) 7.49-7.53 (m, 1H)

Intermediate 2: tert-butyl 5'-acetyl-3'H-spiro[azetidine-3,1'-isobenzofuran]-1-carboxylate

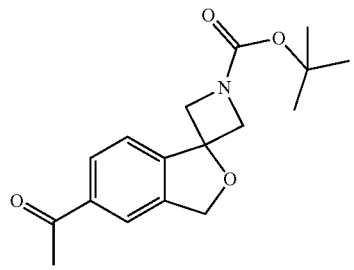 [SMILES: CC(=O)c1ccc2c(c1)COC21CN(C(=O)OC(C)(C)C)C1]

In a scintillation vial containing 15 mL of ethanol was added Pd(OAc)$_2$ (8.3 mg, 0.037 mmol) and DPPP (31 mg, 0.073 mmol). The reaction vessel was purged with argon, capped, and heated to 60° C. for 18 hours. To this was added tert-butyl 5'-bromo-3'H-spiro[azetidine-3,1'-isobenzofuran]-1-carboxylate (250 mg, 0.74 mmol) and triethyl amine(0.21 mL, 1.5 mmol) and the mixture was heated to 90° C. for 5 minutes. Butyl vinyl ether (0.2 mL, 1.5 mmol) was added and the reaction mixture was heated to 90° C. for 4 hours under argon. The reaction mixture was cooled to room temperature and 1.0 N HCl (21 mL) was added and stirred for 2 h at RT. The reaction was neutralized with sat-NaHCO$_3$ and extracted with EtOAc. The organic phase was concentrated and the residue was purified using 40 g Redi-Sep column, eluting with 0 to 40% ethyl acetate in heptanes, to yield 0.17 g of tert-butyl 5'-acetyl-3'H-spiro[azetidine-3,1'-isobenzofuran]-1-carboxylate. H-NMR (400 MHz, CDCl$_3$) δ ppm 7.99 (d, 1H, J=8.0 Hz), 7.82 (s, 1H), 7.57 (d, 1H, J=8.0 Hz), 5.16 (s, 2H), 4.34 (d, 2H, J=9.5 Hz), 4.15 (d, 2H, J=9.5 Hz), 2.63 (s, 3H), 1.49 (s, 9H).

Intermediate 3: 1-(4-chloro-3,5-difluorophenyl)-2,2,2-trifluoroethanone

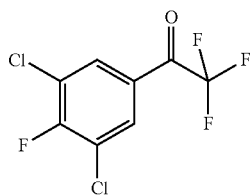 [SMILES: O=C(c1cc(Cl)c(F)c(Cl)c1)C(F)(F)F]

5-Bromo-2-fluoro-1,3-dichlorobenzene (7.0 g, 28.7 mmol) was stirred at room temperature in THF (50 mL) under argon and isopropylmagenesium chloride lithium chloride complex (24.3 mL, 1.3 M in THF, 1.1 eq) was added over 1 min and stirred at RT for 30 min. To this was added piperidine trifluoroacetamide (5.6 mL, 1.32 eq) over about 1 minute at 0° C. and the reaction was stirred at room temperature for 2 h. The reaction was quenched with aqueous saturated NH$_4$Cl (50 mL) and extracted with MTBE (2×50 mL). Solvents were removed under reduced pressure and the crude product was purified using 12 g Redi-Sep column, eluting with 0 to 50% ethyl acetate in heptanes, to yield 3.5 g of 1-(4-chloro-3,5-difluorophenyl)-2,2,2-trifluoroethanone. H-NMR (400 MHz, CDCl$_3$) δ ppm 8.06 (dd, 2H, J, =6.2 Hz, J$_2$=0.9 Hz).

Intermediate 4: tert-butyl 5'-[3-(3,5-dichloro-4-fluorophenyl)-4,4,4-trifluorobut-2-enoyl]-3'H-spiro[azetidine-3,1'-isobenzofuran]-1-carboxylate

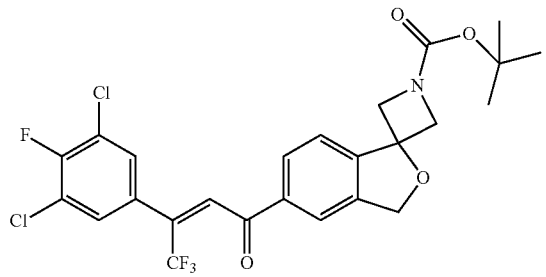 [SMILES: CC(C)(C)OC(=O)N1CC2(C1)OCc1cc(C(=O)/C=C(/c3cc(Cl)c(F)c(Cl)c3)C(F)(F)F)ccc12]

The starting materials, tert-butyl 5'-acetyl-3'H-spiro[azetidine-3,1'-isobenzofuran]-1-carboxylate (5.5 g, 18.1 mmol), 1-(4-chloro-3,5-difluorophenyl)-2,2,2-trifluoroethanone (5.44 g, 1.15 eq), were dissolved in a solvent mixture of toluene and a,a,a-trifluorotoluene (40 mL, 1:1, vol/vol) in a 100 mL three necked round bottom flask equipped with a Dean-Stark head and a condenser on top on one neck and a nitrogen inlet on another. The reaction mixture was heated to 110° C. and cesium carbonate (0.5 g) was added. The reaction mixture was heated for 1 h and then another 0.1 g of cesium carbonate was added and heating was continued for another 1 h under a very slow stream of nitrogen. TLC analysis showed still starting material left and another 0.1 g cesium carbonate was added and heating continued for another 1 h. This process was repeated three more times (total amount of cesium carbonate=1.0 g, total reaction time=6 h). The reaction mixture was cooled to room temperature, filtered through a short path of silica gel, rinsed with MTBE, and concentrated. The crude product was purified using flash silica gel column chromatography (330 g RediSep column, eluting with 0 to 20% ethyl acetate in heptanes) to yield 8 g of tert-butyl 5'-[3-(3,5-dichloro-4-fluorophenyl)-4,4,4-trifluorobut-2-enoyl]-3'H-spiro[azetidine-3,1'-isobenzofuran]-1-carboxylate. H-NMR (400 MHz, CDCl$_3$) δ ppm 7.86 (d, 1H, J=8.0 Hz), 7.69 (s, 1H), 7.58 (d, 1H, J=8.0 Hz), 7.42 (d, 1H, J=1.4 Hz), 7.25 (d, 2H, J=6.1 Hz), 5.14 (s, 2H), 4.34 (d, 2H, J=9.5 Hz), 4.13 (d, 2H, J=9.5 Hz), 1.49 (s, 9H).

Intermediate 5: tert-butyl 5'-[3-(3,5-dichloro-4-fluorophenyl)-3-thioacetyl-4,4,4-trifluorobutanoyl]-3'H-spiro[azetidine-3,1'-isobenzofuran]-1-carboxylate

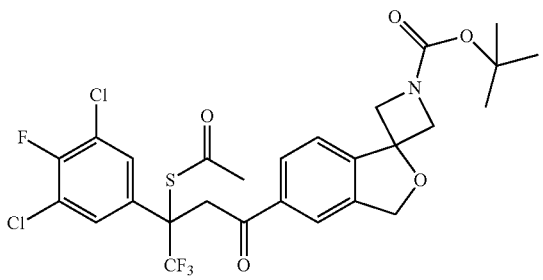 [SMILES: CC(=O)SC(CC(=O)c1ccc2c(c1)COC21CN(C(=O)OC(C)(C)C)C1)(c1cc(Cl)c(F)c(Cl)c1)C(F)(F)F]

The starting material, tert-butyl 5'-[3-(3,5-dichloro-4-fluorophenyl)-4,4,4-trifluorobut-2-enoyl]-3'H-spiro[azetidine-3,1'-isobenzofuran]-1-carboxylate (3.0 g, 6.0 mmoL), was dissolved in dichloromethane (14 mL) and to this solution were added thioacetic acid (2.6 mL, 6.0 eq) and 2 drops of triethylamine and the resulting mixture was stirred at room temperature for 96 h under argon. Solvents were removed under reduced pressure and the crude product was purified via flash silica gel chromatography to yield 1.3 g of tert-butyl 5'-[3-(3,5-dichloro-4-fluorophenyl)-3-thioacetyl-4,4,4-trifluorobutanoyl]-3'H-spiro[azetidine-3,1'-isobenzofuran]-1-carboxylate. HNMR (400 MHz, CDCl$_3$) δ ppm 8.01 (d, 1H, J=8.0 Hz), 7.82 (s, 1H), 7.60 (d, 1H, J=8.0 Hz), 7.45 (d, 1H, J=5.8 Hz), 5.23 (d, 1H, J=18.5 Hz), 5.17 (s, 2H), 4.35 (d, 2H, J=9.7 Hz), 4.15 (d, 2H, J=9.7 Hz), 3.97 (d, 1H, J=18.5 Hz), 2.33 (s, 3H), 1.50 (s, 9H).

Intermediate 6: tert-butyl 5'-[3-(3,5-dichloro-4-fluorophenyl)-3-mercapto-4,4,4-trifluorobutanoyl]-3'H-spiro[azetidine-3,1'-isobenzofuran]-1-carboxylate

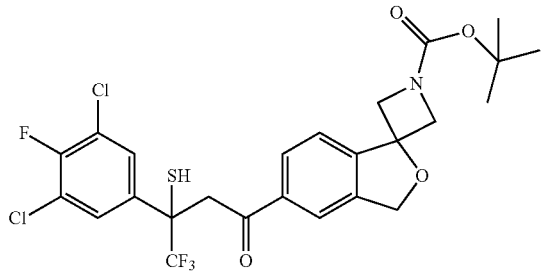 [SMILES: CC(C)(C)OC(=O)N1CC2(C1)OCc1cc(C(=O)CC(S)(c3cc(Cl)c(F)c(Cl)c3)C(F)(F)F)ccc12]

To a solution of tert-butyl 5'-[3-(3,5-dichloro-4-fluorophenyl)-3-thioacetyl-4,4,4-trifluorobutanoyl]-3'H-spiro[azetidine-3,1'-isobenzofuran]-1-carboxylate (1.3 g, 2.3 mmol) in methanol (23 mL) was added a solution of 25 wt. % sodium methoxide in methanol (0.58 mL, 1.1 eq) and the resulting mixture was stirred at room temperature for 30 min under nitrogen. The reaction was quenched with HOAc (0.13 mL), diluted with ethyl acetate, and washed with brine. The organic extract was concentrated and subjected to silica gel column chromatography (0 to 30% ethyl acetate in heptane) to yield 530 mg of the thiol product with trace amount of tert-butyl 5'-[3-(3,5-dichloro-4-fluorophenyl)-3-mercapto-4,4,4-trifluorobutanoyl]-3'H-spiro[azetidine-3,1'-isobenzofuran]-1-carboxylate. HNMR (400 MHz, CDCl$_3$) δ ppm 7.97 (d, 1H, J=8.0 Hz), 7.78 (s, 1H), 7.63 (d, 2H, J=5.8 Hz), 7.61 (d, 1H, J=8.0 Hz), 5.17 (s, 2H), 4.35 (d, 2H, J=9.7 Hz), 4.29 (d, 1H, J=18.5 Hz), 4.15 (d, 2H, J=9.7 Hz), 4.00 (d, 1H, J=18.5 Hz), 3.31 (s, 1H), 1.50 (s, 9H).

Intermediate 7: tert-butyl 6-[5-(3,5-dichloro-4-fluoro-phenyl)-3-hydroxy-5-(trifluoromethyl)isothiazolidin-3-yl]spiro[1H-isobenzofuran-3,3'-azetidine]-1'-carboxylate

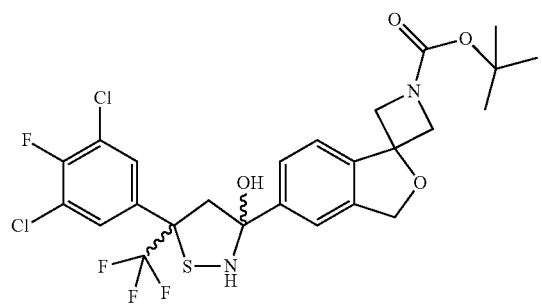 [SMILES: CC(C)(C)OC(=O)N1CC2(C1)OCc1cc(C3(O)CC(c4cc(Cl)c(F)c(Cl)c4)(C(F)(F)F)SN3)ccc12]

To a solution of Intermediate 6 (530 mg) in a solution of potassium hydroxide (182 mg) in water (9 mL) was added a solution of hydroxylamine-O-sulfonic acid (183 mg, 2 eq) in a solution of potassium hydroxide (273 mg) in water (18 mL) and the resulting mixture was stirred at room temperature for 30 min under nitrogen. The mixture was diluted with ethyl acetate and washed with brine. The organic extract was concentrated and subjected to silica gel column chromatography (0 to 30% ethyl acetate in heptane) to yield 150 mg of Intermediate 7 as a mixture of diastereomers.

Intermediate 8: 6-[5-(3,5-dichloro-4-fluoro-phenyl)-5-(trifluoromethyl)-4H-isothiazol-3-yl]spiro[1H-isobenzofuran-3,3'-azetidine]

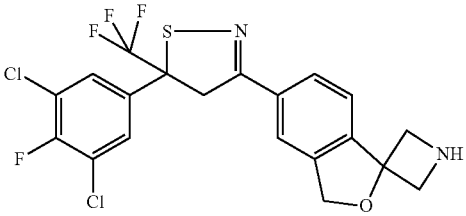 [SMILES: Fc1c(Cl)cc(C2(C(F)(F)F)CC(c3ccc4c(c3)COC43CNC3)=NS2)cc1Cl]

To a solution of intermediate 7 in ethylacetate/toluene (1/1), p-toluene sulfonic acid (3 eq) was added. The reaction was stirred and heated at 100° C. for 1 h. Solvents are removed under vacuum. The crude was subjected to reverse phase column chromatography (10 to 100% acetonitrile in aqueous HCl (0.1% vol)) to afford 6-[5-(3,5-dichloro-4-fluoro-phenyl)-5-(trifluoromethyl)-4H-isothiazol-3-yl]spiro[1H-isobenzofuran-3,3'-azetidine].

Compound 1: 1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-3,3,3-trifluoro-propan-1-one

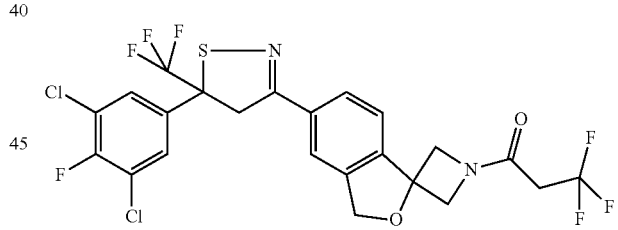

To a solution of intermediate 8 (16 mg, 33.5 nmol, 1 eq) in DMF (1.2 mL), N-methylmorpholine (0.2 mmol, 6 eq), 3,3,3-trifluoropropionic acid (0.1 mmol, 3 eq), HOBt (15.4 mg, 3 eq) and EDCI (19.3 mg, 3 eq) were added. Reaction was stirred at room temperature overnight. Reaction was quenched with water (5 drops) and diluted in DMSO. The solution was directly submitted to reverse phase column chromatography (15 to 100% methanol in water). 11 mg of 1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-3,3,3-trifluoro-propan-1-one were obtained.

$^1$H NMR (400 MHz, CD$_3$OD) δ ppm 4.16 (d, J=18.16 Hz, 1H) 4.27-4.37 (m, 2H) 4.43 (d, J=18.16 Hz, 1H) 4.52-4.63 (m, 2H) 5.17 (s, 2H) 7.59-7.63 (m, 3H) 7.78 (s, 1H) 7.92 (d, J=7.96 Hz, 1H)

Example 2

6-[5-(3,5-dichloro-4-fluoro-phenyl)-5-(trifluoromethyl)-4H-isothiazol-3-yl]-N-(2,2,2-trifluoroethyl)spiro[1H-isobenzofuran-3,3'-azetidine]-1'-carboxamide

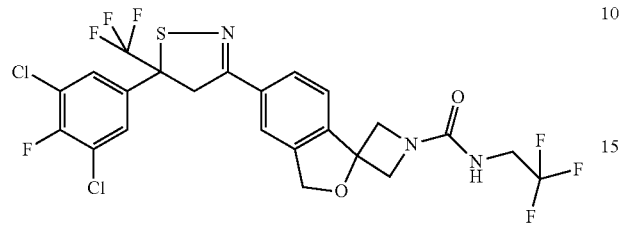

To a solution of intermediate 8 (18 mg, 37.7 nmol, 1 eq) in DCM (1.5 mL), TEA (75.4 nmol, 2 eq) and 2,2,2-trifluoroethylisocyanate (5.2 mg, 1.1 eq) were added. Reaction was stirred at room temperature overnight. Solvents were evaporated under low pressure to lead to a white solid. Solubilized in EtOAc, it was washed with water and concentrated under vacuum. This was subjected to silica gel column chromatography (10 to 100% ethyl acetate in heptane). 15 mg of 6-[5-(3,5-dichloro-4-fluoro-phenyl)-5-(trifluoromethyl)-4H-isothiazol-3-yl]-N-(2,2,2-trifluoroethyl)spiro[1H-isobenzofuran-3,3'-azetidine]-1'-carboxamide were obtained.

$^1$H NMR (400 MHz, CD$_3$OD) δ ppm 3.85 (q, J=9.39 Hz, 2H) 4.07-4.13 (m, 1H) 4.15 (d, J=18.35 Hz, 1H) 4.19-4.23 (m, 2H) 4.29-4.33 (m, 2H) 4.43 (d, J=18.16 Hz, 1H) 5.15 (s, 2H) 7.56-7.63 (m, 3H) 7.78 (s, 1H) 7.91 (d, J=8.00 Hz, 1H)

Example 3

6-[5-(3,5-dichloro-4-fluoro-phenyl)-5-(trifluoromethyl)-4H-isothiazol-3-yl]-1'-(4-fluorophenyl)sulfonyl-spiro[1H-isobenzofuran-3,3'-azetidine]

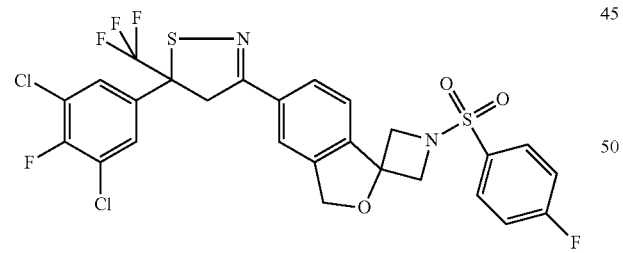

To a solution of intermediate 8 (14.3 mg, 30 nmol, 1 eq) in 1.2-dichloroethane (1.5 mL), TEA (90 nmol, 3 eq) and 4-fluorobenzenesulfonyl chloride (6.4 mg, 1.1 eq) were added under nitrogen atmosphere. Reaction was stirred at room temperature for 1 h. Solvents were evaporated under low pressure. Crude was solubilized in EtOAc; organic layer was washed with water and concentrated under vacuum. The oil obtained was subjected to silica gel column chromatography (8 to 100% ethyl acetate in heptane) to afford 6-[5-(3,5-dichloro-4-fluoro-phenyl)-5-(trifluoromethyl)-4H-isothiazol-3-yl]-1'-(4-fluorophenyl)sulfonyl-spiro[1H-isobenzofuran-3,3'-azetidine].

$^1$H NMR (400 MHz, CD$_3$OD) δ ppm 3.86 (d, J=17.57 Hz, 1H) 4.06 (q, J=8.98 Hz, 4H) 4.21 (d, J=17.57 Hz, 1H) 5.05 (s, 2H) 7.33 (t, J=8.54 Hz, 2H) 7.39 (d, J=5.86 Hz, 2H) 7.50 (d, J=8.05 Hz, 1H) 7.64 (s, 1H) 7.72 (d, J=8.05 Hz, 1H) 7.92-7.97 (m, 2H).

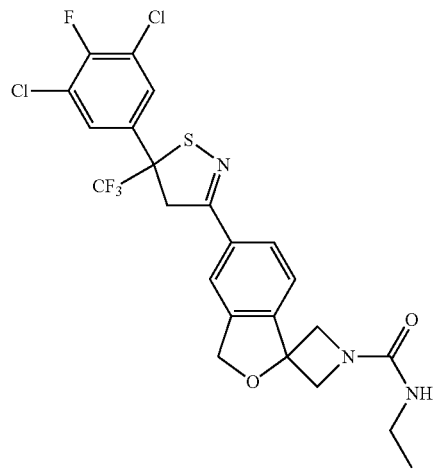 [SMILES: CCNC(=O)N1CC2(C1)OCc1cc(C3=NSC(c4cc(Cl)c(F)c(Cl)c4)(C(F)(F)F)C3)ccc12]

Example 4

6-[5-(3,5-dichloro-4-fluoro-phenyl)-5-(trifluoromethyl)-4H-isothiazol-3-yl]-N-ethyl-spiro[1H-isobenzofuran-3,3'-azetidine]-1'-carboxamide To a solution of intermediate 8 (22 mg, 4.6×10$^{-2}$ mmol) and EtN(i-Pr)$_2$ (9.0 mL, 5.1×10$^{-2}$ mmol) in THF (0.46 mL) was added ethylisocyanate (4.0 mL, 5.1×10$^{-2}$ mmol). Reaction stirred at room temperature for 16 h. MeOH (0.5 mL) was added and reaction was allowed to stir for 20 min. before it was concentrated in vacuo. The isolated residue was chromatographed over silica gel (0 to 100% EtOAc in heptanes) to give 21 mg of 6-[5-(3,5-dichloro-4-fluoro-phenyl)-5-(trifluoromethyl)-4H-isothiazol-3-yl]-N-ethyl-spiro[1H-isobenzofuran-3,3'-azetidine]-1'-carboxamide (83%). 1H NMR (400 MHz, CHLOROFORM-d) δ ppm 7.75 (d, J=8.0 Hz, 1H), 7.66 (s, 1H), 7.55 (d, J=8.0 Hz, 1H), 7.39 (d, J=5.9 Hz, 2H), 5.15 (s, 2H), 4.34 (d, J=8.8 Hz, 2H), 4.23 (d, J=17.5 Hz, 1H), 4.19-4.10 (m, 3H), 3.88 (d, J=17.5 Hz, 1H), 3.36-3.26 (m, 2H), 1.18 (t, J=7.2 Hz, 3H.

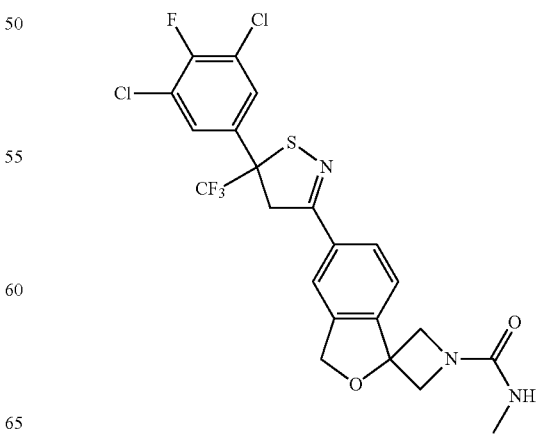

Example 5

6-[5-(3,5-dichloro-4-fluoro-phenyl)-5-(trifluoromethyl)-4H-isothiazol-3-yl]-N-methyl-spiro[1H-isobenzofuran-3,3'-azetidine]-1'-carboxamide To a solution of intermediate 8 (50 mg, 0.10 mmol) and urea 3 (14 mg, 0.12 mmol) in DCM (1 mL) was added N-methylmorpholine (14 mL, 0.13 mmol). Reaction stirred at room temperature for 24 h before it was quenched with aq. NaOH (0.25 mL, 1 molar). Mixture stirred for 30 min. before pH was adjusted to approximately 4 with aq. HCl (0.1 molar). Organic layer was separated, washed with sat. aq. NaCl, dried over $Na_2SO_4$, filtered and concentrated in vacuo. The resultant residue was chromatographed on silica gel (20 to 100% EtOAc in heptanes) to give 39 mg of 6-[5-(3,5-dichloro-4-fluoro-phenyl)-5-(trifluoromethyl)-4H-isothiazol-3-yl]-N-methyl-spiro[1H-isobenzofuran-3,3'-azetidine]-1'-carboxamide (70%). 1H NMR (400 MHz, CHLOROFORM-d) δ ppm 7.79-7.72 (m, 1H), 7.66 (s, 1H), 7.54 (d, J=8.0 Hz, 1H), 7.39 (d, J=5.9 Hz, 2H), 5.15 (s, 2H), 4.34 (d, J=8.8 Hz, 2H), 4.22 (d, J=17.5 Hz, 1H), 4.16-4.13 (m, 2H), 3.88 (d, J=17.6 Hz, 1H), 2.86 (d, J=4.8 Hz, 3H).

Example 6

1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-3,3,3-trifluoro-propan-1-one To a solution of intermediate 8 (213 mg, 0.446 mmol) in DMF (2.5 mL) was added EtN(i-Pr)$_2$ (0.47 mL, 2.7 mmol), 3,3,3-trifluoropropionic acid (0.12 mL, 1.3 mmol), HOBt hydrate (180 mg, 1.3 mmol), and EDCI.HCl (260 mg, 1.3 mmol). Reaction stirred at room temp for 3 h. before it was poured into water. The suspension was extracted 3× EtOAc and combined organic layers were washed 2× saturated aq. NaHCO$_3$, 2×10% aq. LiCl and 1× saturated aq. NaCl. The solution was dried over Na$_2$SO$_4$, filtered and concentrated in vacuo. The residue was chromatographed on silica gel (0 to 50% EtOAc in heptane) to give 199 mg of 1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-3,3,3-trifluoro-propan-1-one as a white solid (76%). $^1$H NMR (400 MHz, CHLOROFORM-d) δ ppm 3.08 (qd, J=10.28, 2.29 Hz, 2H) 3.88 (d, J=17.42 Hz, 1H) 4.23 (d, J=17.52 Hz, 1H) 4.31-4.37 (m, 1H) 4.39-4.48 (m, 2H) 4.60 (d, J=8.93 Hz, 1H) 5.18 (s, 2H) 7.39 (d, J=5.86 Hz, 2H) 7.48 (d, J=7.96 Hz, 1H) 7.69 (d, J=4.78 Hz, 1H) 7.77 (dd, J=7.66, 4.44 Hz, 1H).

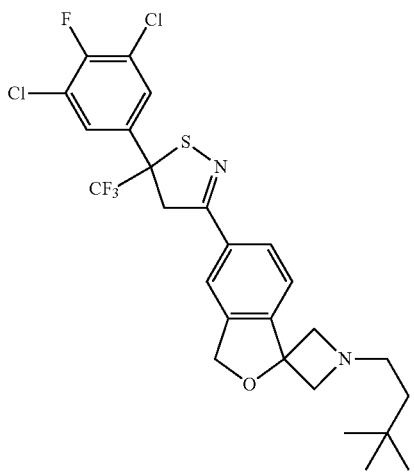 [SMILES: CC(C)(C)CCN1CC2(C1)OCc1cc(C3=NSC(c4cc(Cl)c(F)c(Cl)c4)(C(F)(F)F)C3)ccc12]

Example 7

6-[5-(3,5-dichloro-4-fluoro-phenyl)-5-(trifluoromethyl)-4H-isothiazol-3-yl]-1'-(3,3- butyl)spiro[1H-isobenzofuran-3,3'-azetidine]

To a solution of intermediate 8 (26 mg, 0.055 mmol) in DCM (0.33 mL) was added a solution of 3,3-dimethyl-butyraldehyde (14 mL, 0.11 mmol) and acetic acid (4.8 mL, 0.083 mmol) in DCM (0.33 mL) followed by NaBH$_4$ (26 mg, 0.12 mmol). Reaction stirred at room temperature for 17 h before it was quenched with sat. aq. NaHCO$_3$ (1 mL). The mixture was extracted with 2× EtOAc. The combined organic layers were washed with water, sat. aq. NaCl, dried over Na$_2$SO$_4$, filtered and concentrated in vacuo. The residue was chromatographed over silica gel (15 to 100% EtOAc in heptane) to give 20 mg of 6-[5-(3,5-dichloro-4-fluoro-phenyl)-5-(trifluoromethyl)-4H-isothiazol-3-yl]-1'-(3,3-dimethylbutyl)spiro[1H-isobenzofuran-3,3'-azetidine] (65%). 1H NMR (400 MHz, CHLOROFORM-d) δ ppm 7.79-7.69 (m, 2H), 7.62 (s, 1H), 7.40 (d, J=5.9 Hz, 2H), 5.10 (s, 2H), 4.23 (d, J=17.5 Hz, 1H), 3.88 (d, J=17.5 Hz, 1H), 3.63 (d, J=8.4 Hz, 2H), 3.38-3.34 (m, 2H), 2.59-2.53 (m, 2H), 1.35-1.30 (m, 2H), 0.94 (s, 9H).

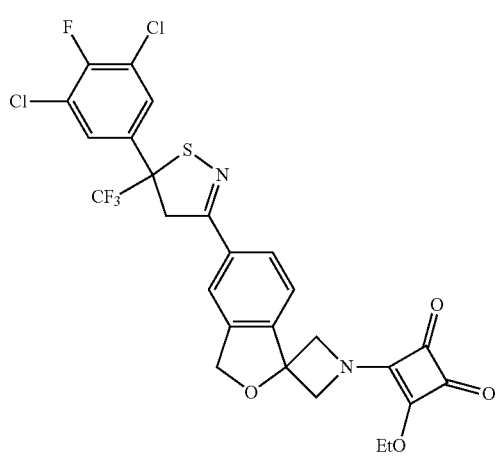 [SMILES: CCOc1c(N2CC3(C2)OCc2cc(C4=NSC(c5cc(Cl)c(F)c(Cl)c5)(C(F)(F)F)C4)ccc23)c(=O)c1=O]

Example 8

3-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-4-ethoxy-cyclobut-3-ene-1,2-dione To a solution of intermediate 8 (29 mg, 0.060 mmol) in EtOH (0.3 mL) was added 3,4-diethoxy-3-cyclobutene-1,2-dione (8.8 mL, 0.060 mmol). A suspension formed and additional EtOH (0.3 mL) was added. The reaction stirred at room temperature for 18 h before additional 3,4-diethoxy-3-cyclobutene-1,2-dione (2.2 mL, 0.015 mmol) was added. Reaction stirred at room temperature an additional 3 h before it was concentrated in vacuo. The residue was chromatographed over silica gel (0 to 100% EtOAc in heptane) to give 27 mg of 3-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-4-ethoxy-cyclobut-3-ene-1,2-dione (74%). 1H NMR (400 MHz, CHLOROFORM-d) δ ppm 7.80 (d, J=7.9 Hz, 1H), 7.69 (s, 1H), 7.59 (d, J=8.0 Hz, 1H), 7.39 (d, J=5.9 Hz, 2H), 5.18 (s, 2H), 4.89-4.62 (m, 6H), 4.23 (d, J=17.6 Hz, 1H), 3.89 (d, J=17.6 Hz, 1H), 1.46 (t, J=7.1 Hz, 3H).

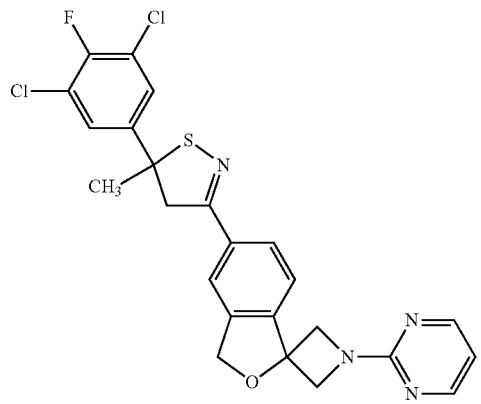 [SMILES: CC1(c2cc(Cl)c(F)c(Cl)c2)CC(c2ccc3c(c2)COC32CN(c3ncccn3)C2)=NS1]

Example 9

6-[5-(3,5-dichloro-4-fluoro-phenyl)-5-(trifluoromethyl)-4H-isothiazol-3-yl]-1'-pyrimidin-2-yl-spiro[1H-isobenzofuran-3,3'-azetidine]

To a mixture of intermediate 8 (22 mg, 0.045 mmol) and 2-(methylsulfonyl)pyrimidine (3.6 mg, 0.054 mmol) was added i-PrOH (1 mL). The mixture was irradiated with microwaves (250 watts, 110° C., 200 psi) for 90 min. The reaction was allowed to cool to room temperature and concentrated in vacuo. The residue was chromatographed over silica gel (0 to 100% EtOAc in heptane) to give 15 mg of 6-[5-(3,5-dichloro-4-fluoro-phenyl)-5-(trifluoromethyl)-4H-isothiazol-3-yl]-1'-pyrimidin-2-yl-spiro[1H-isobenzofuran-3,3'-azetidine] (59%). 1H NMR (400 MHz, CHLOROFORM-d) δ ppm 8.39 (d, J=4.8 Hz, 2H), 7.75 (d, J=8.0 Hz, 1H), 7.69 (s, 1H), 7.58 (d, J=8.0 Hz, 1H), 7.39 (d, J=5.9 Hz, 2H), 6.64 (t, J=4.8 Hz, 1H), 5.21 (s, 2H), 4.53 (d, J=10.0 Hz, 2H), 4.39 (d, J=9.6 Hz, 2H), 4.23 (d, J=17.5 Hz, 1H), 3.89 (d, J=17.6 Hz, 1H).

By proceeding in a similar fashion to Examples 1-9, the following compounds were prepared:

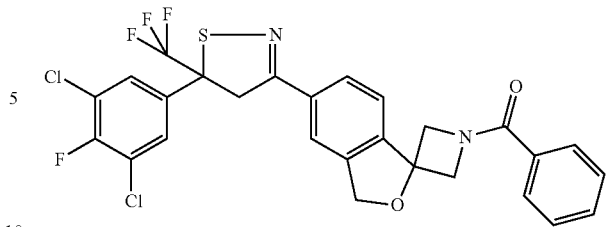

Example 10

[6-[5-(3,5-dichloro-4-fluoro-phenyl)-5-(trifluoromethyl)-4H-isothiazol-3-yl]spiro[1H-isobenzofuran-3,3'-azetidine]-1'-yl]-phenyl-methanone 1H NMR (400 MHz, CD$_3$OD) δ ppm 4.15 (d, J=18.21 Hz, 1H) 4.43 (d, J=18.16 Hz, 1H) 4.49 (br. s., 2H) 4.59-4.72 (m, 2H) 5.17 (d, J=2.59 Hz, 2H) 7.48-7.51 (m, 2H) 7.52-7.55 (m, 1H) 7.60 (d, J=6.05 Hz, 2H) 7.64 (d, J=8.00 Hz, 1H) 7.71-7.75 (m, 2H) 7.78 (s, 1H) 7.91 (d, J=8.10 Hz, 1H)

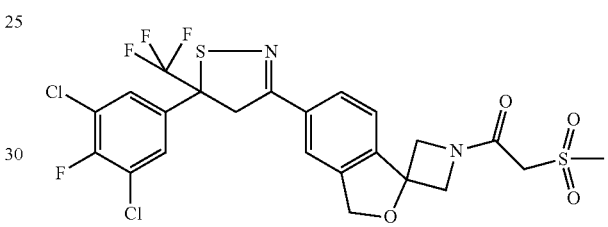

Example 11

1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-2-methylsulfonyl-ethanone LCMS m/e 596 (M+H); 1H NMR (400 MHz, CD$_3$OD) δ ppm 3.15 (s, 3H) 4.08-4.21 (m, 3H) 4.25-4.37 (m, 2H) 4.41 (d, J=18.11 Hz, 1H) 4.61-4.72 (m, 2H) 5.15 (s, 2H) 7.59 (d, J=6.05 Hz, 2H) 7.63 (d, J=8.05 Hz, 1H) 7.76 (s, 1H) 7.88 (d, J=8.10 Hz, 1H).

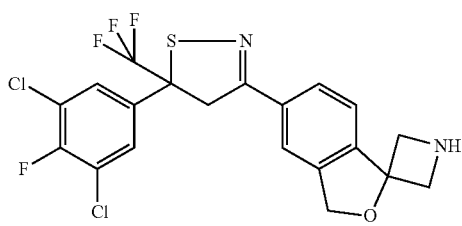 [SMILES: Fc1c(Cl)cc(C2(C(F)(F)F)CC(c3ccc4c(c3)COC43CNC3)=NS2)cc1Cl]

Example 12

6-[5-(3,5-dichloro-4-fluoro-phenyl)-5-(trifluoromethyl)-4H-isothiazol-3-yl]spiro[1H-isobenzofuran-3,3'-azetidine]

LCMS m/e 477 (M+H); 1H NMR (400 MHz, CHLOROFORM-d) δ ppm 7.87-7.82 (m, 1H), 7.75 (d, J=8.7 Hz, 1H), 7.64 (s, 1H), 7.39 (d, J=5.9 Hz, 2H), 5.12 (s, 2H), 4.28-4.18 (m, 3H), 3.93-3.78 (m, 3H), 2.84 (br. s., 1H)

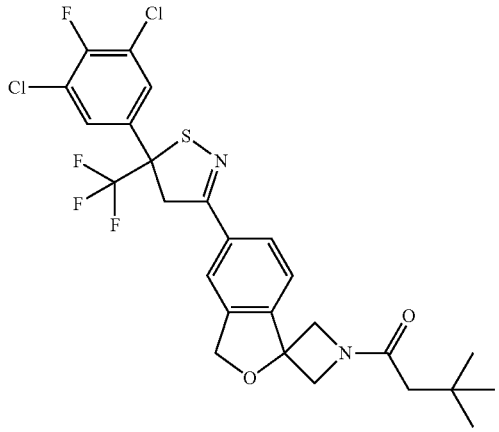 [SMILES: CC(C)(C)CC(=O)N1CC2(C1)OCc1cc(C3=NSC(c4cc(Cl)c(F)c(Cl)c4)(C(F)(F)F)C3)ccc12]

Example 13

1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-3,3-dimethyl-butan-1-one LCMS m/e 575 (M+H); 1H NMR (400 MHz, CHLOROFORM-d) δ ppm 7.76 (t, J=6.9 Hz, 1H), 7.67 (d, J=6.3 Hz, 1H), 7.46 (d, J=8.0 Hz, 1H), 7.39 (d, J=5.9 Hz, 2H), 5.16 (s, 2H), 4.52 (d, J=9.0 Hz, 1H), 4.41-4.36 (m, 1H), 4.33 (d, J=9.1 Hz, 1H), 4.27 (d, J=10.8 Hz, 1H), 4.22 (d, J=17.5 Hz, 1H), 3.88 (d, J=17.5 Hz, 1H), 2.09 (s, 2H), 1.10 (s, 9H)

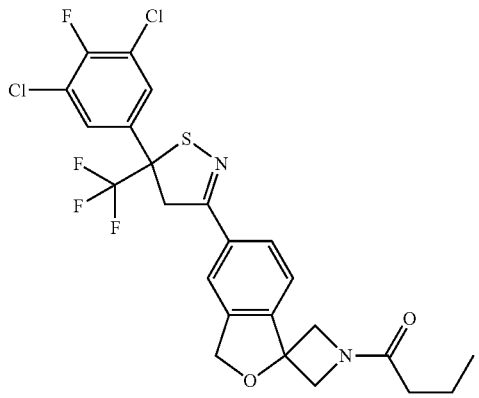 [SMILES: CCCC(=O)N1CC2(C1)OCc1cc(C3=NSC(c4cc(Cl)c(F)c(Cl)c4)(C(F)(F)F)C3)ccc12]

Example 14

1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]butan-1-one LCMS m/e 547 (M+H); 1H NMR (400 MHz, CHLOROFORM-d) δ ppm 7.80-7.73 (m, 1H), 7.67 (d, J=5.4 Hz, 1H), 7.48 (d, J=8.0 Hz, 1H), 7.39 (d, J=5.9 Hz, 2H), 5.17 (s, 2H), 4.51 (d, J=9.1 Hz, 1H), 4.41-4.36 (m, 1H), 4.32 (d, J=9.1 Hz, 1H), 4.27 (d, J=10.7 Hz, 1H), 4.23 (d, J=17.5 Hz, 1H), 3.88 (d, J=17.5 Hz, 1H), 2.17 (t, J=7.4 Hz, 2H), 1.72 (sxt, J=7.4 Hz, 2H), 1.00 (t, J=7.4 Hz, 3H)

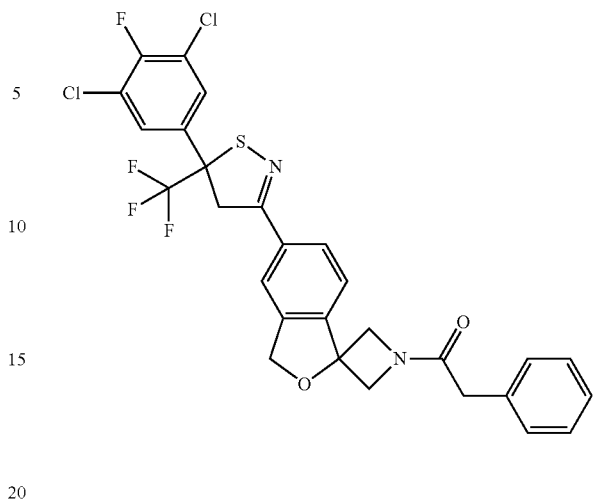

Example 15

1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-2-phenyl-ethanone LCMS m/e 595 (M+H); 1H NMR (400 MHz, CHLOROFORM-d) δ ppm 7.71 (t, J=6.8 Hz, 1H), 7.64 (d, J=5.9 Hz, 1H), 7.41-7.28 (m, 8H), 5.18-5.08 (m, 2H), 4.47 (d, J=9.3 Hz, 1H), 4.40 (d, J=10.7 Hz, 1H), 4.31-4.16 (m, 3H), 3.86 (d, J=17.5 Hz, 1H), 3.65-3.54 (m, 2H)

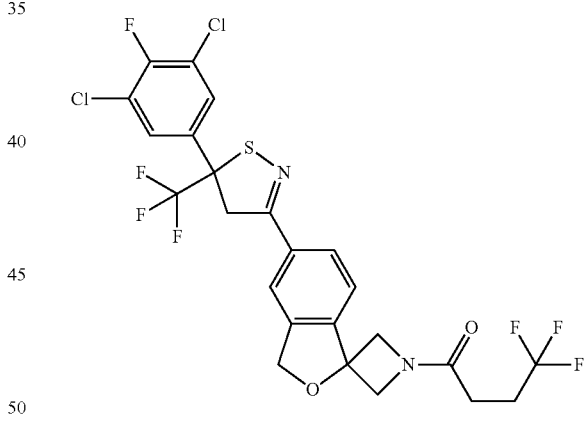

Example 16

1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-4,4,4-trifluoro-butan-1-one LCMS m/e 601 (M+H); 1H NMR (400 MHz, CHLOROFORM-d) δ ppm 7.77 (dd, J=2.6, 7.8 Hz, 1H), 7.68 (d, J=3.0 Hz, 1H), 7.48 (d, J=8.0 Hz, 1H), 7.39 (d, J=5.9 Hz, 2H), 5.18 (s, 2H), 4.53 (d, J=8.9 Hz, 1H), 4.44-4.38 (m, 1H), 4.35 (d, J=9.1 Hz, 1H), 4.32-4.27 (m, 1H), 4.23 (d, J=17.5 Hz, 1H), 3.88 (d, J=17.5 Hz, 1H), 2.62-2.40 (m, 4H)

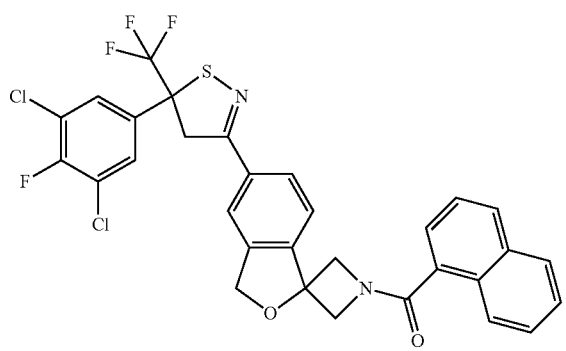 [SMILES: O=C(c1cccc2ccccc12)N1CC2(C1)OCc1cc(C3=NSC(c4cc(Cl)c(F)c(Cl)c4)(C(F)(F)F)C3)ccc12]

Example 17

[6-[5-(3,5-dichloro-4-fluoro-phenyl)-5-(trifluoromethyl)-4H-isothiazol-3-yl]spiro[1H-isobenzofuran-3,3'-azetidine]-1'-yl]-(1-naphthyl)methanone LCMS m/e 631 (M+H); 1H NMR (400 MHz, CHLOROFORM-d) δ ppm 8.24 (d, J=8.5 Hz, 1H), 7.91 (dd, J=8.2, 12.5 Hz, 2H), 7.77 (d, J=8.2 Hz, 1H), 7.69-7.60 (m, 3H), 7.60-7.47 (m, 3H), 7.38 (d, J=5.9 Hz, 2H), 5.23-5.05 (m, 2H), 4.73-4.56 (m, 2H), 4.35 (d, J=10.1 Hz, 1H), 4.21 (d, J=17.6 Hz, 1H), 4.10-4.03 (m, 1H), 3.87 (d, J=17.5 Hz, 1H)

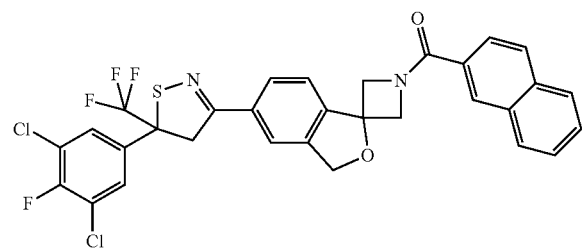 [SMILES: O=C(c1ccc2ccccc2c1)N1CC2(C1)OCc1cc(C3=NSC(c4cc(Cl)c(F)c(Cl)c4)(C(F)(F)F)C3)ccc12]

Example 18

[(3Z,4Z)-4-allylidene-3-ethylidene-cyclohexa-1,5-dien-1-yl]-[6-[5-(3,5-dichloro-4-fluoro-phenyl)-5-(trifluoromethyl)-4H-isothiazol-3-yl]spiro[1H-isobenzofuran-3,3'-azetidine]-1'-yl]methanone LCMS m/e 631 (M+H); 1H NMR (400 MHz, CHLOROFORM-d) δ ppm 8.22 (s, 1H), 7.95-7.87 (m, 3H), 7.83-7.70 (m, 2H), 7.68 (s, 1H), 7.63-7.52 (m, 3H), 7.39 (d, J=5.9 Hz, 2H), 5.17 (d, J=13.6 Hz, 2H), 4.88-4.60 (m, 2H), 4.59-4.51 (m, 2H), 4.22 (d, J=17.5 Hz, 1H), 3.92-3.84 (m, 1H)

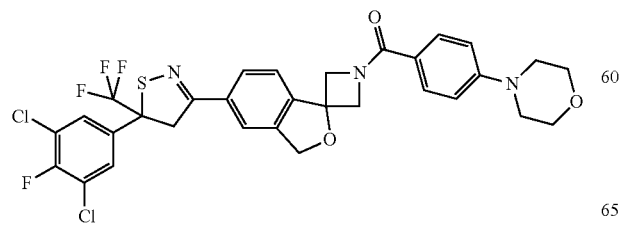

Example 19

[6-[5-(3,5-dichloro-4-fluoro-phenyl)-5-(trifluoromethyl)-4H-isothiazol-3-yl]spiro[1H-isobenzofuran-3,3'-azetidine]-1'-yl]-(4-morpholinophenyl)methanone LCMS m/e 666 (M+H); 1H NMR (400 MHz, CHLOROFORM-d) δ ppm 7.74 (d, J=8.0 Hz, 1H), 7.68 (d, J=9.0 Hz, 3H), 7.51 (d, J=8.0 Hz, 1H), 7.39 (d, J=5.9 Hz, 2H), 6.89 (d, J=8.9 Hz, 2H), 5.17 (s, 2H), 4.81-4.56 (m, 2H), 4.53-4.48 (m, 2H), 4.22 (d, J=17.5 Hz, 1H), 3.91-3.84 (m, 5H), 3.29-3.24 (m, 4H)

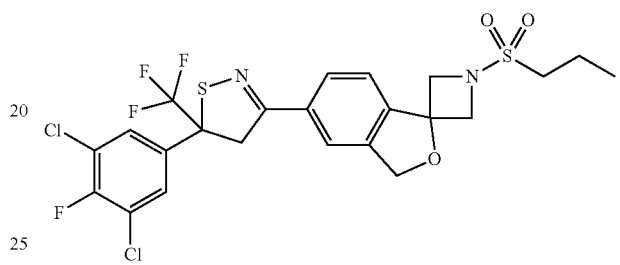

Example 20

6-[5-(3,5-dichloro-4-fluoro-phenyl)-5-(trifluoromethyl)-4H-isothiazol-3-yl]-1'-propylsulfonyl-spiro[1H-isobenzofuran-3,3'-azetidine]

LCMS m/e 583 (M+H); 1H NMR (400 MHz, CHLOROFORM-d) δ ppm 7.77 (d, J=8.8 Hz, 1H), 7.70-7.65 (m, 2H), 7.39 (d, J=5.9 Hz, 2H), 5.15 (s, 2H), 4.36 (d, J=9.3 Hz, 2H), 4.26-4.16 (m, 3H), 3.88 (d, J=17.5 Hz, 1H), 3.07-3.01 (m, 2H), 1.99-1.87 (m, 2H), 1.11 (t, J=7.5 Hz, 3H)

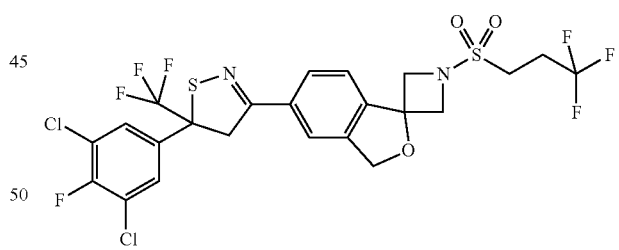

Example 21

6-[5-(3,5-dichloro-4-fluoro-phenyl)-5-(trifluoromethyl)-4H-isothiazol-3-yl]-1'-(3,3,3-trifluoropropylsulfonyl)spiro[1H-isobenzofuran-3,3'-azetidine]

LCMS m/e 635 (M+H); 1H NMR (400 MHz, CHLOROFORM-d) δ ppm 7.78 (d, J=8.0 Hz, 1H), 7.70-7.62 (m, 2H), 7.39 (d, J=5.9 Hz, 2H), 5.18-5.14 (m, 2H), 4.41 (d, J=9.4 Hz, 2H), 4.26-4.19 (m, 3H), 3.88 (d, J=17.6 Hz, 1H), 3.30-3.24 (m, 2H), 2.77-2.64 (m, 2H)

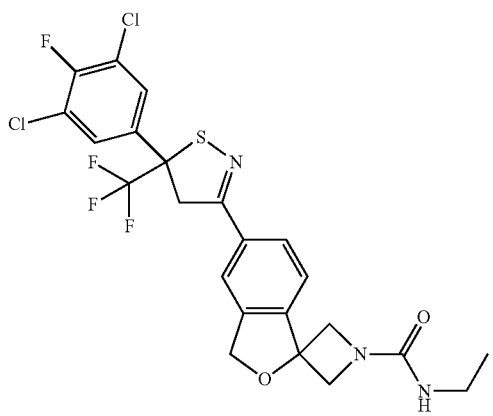 [SMILES: CCNC(=O)N1CC2(C1)OCc1cc(C3=NSC(c4cc(Cl)c(F)c(Cl)c4)(C(F)(F)F)C3)ccc12]

Example 22

6-[5-(3,5-dichloro-4-fluoro-phenyl)-5-(trifluoromethyl)-4H-isothiazol-3-yl]-N-ethyl-spiro[1H-isobenzofuran-3,3'-azetidine]-1'-carboxamide LCMS m/e 548 (M+H); 1H NMR (400 MHz, CHLOROFORM-d) δ ppm 7.75 (d, J=8.0 Hz, 1H), 7.66 (s, 1H), 7.55 (d, J=8.0 Hz, 1H), 7.39 (d, J=5.9 Hz, 2H), 5.15 (s, 2H), 4.34 (d, J=8.8 Hz, 2H), 4.23 (d, J=17.5 Hz, 1H), 4.19-4.10 (m, 3H), 3.88 (d, J=17.5 Hz, 1H), 3.36-3.26 (m, 2H), 1.18 (t, J=7.2 Hz, 3H)

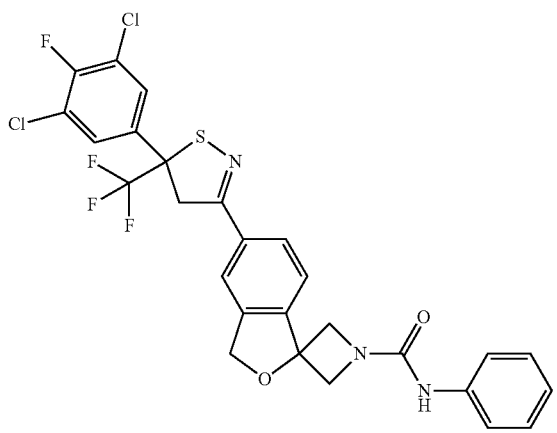 [SMILES: O=C(Nc1ccccc1)N1CC2(C1)OCc1cc(C3=NSC(c4cc(Cl)c(F)c(Cl)c4)(C(F)(F)F)C3)ccc12]

Example 23

6-[5-(3,5-dichloro-4-fluoro-phenyl)-5-(trifluoromethyl)-4H-isothiazol-3-yl]-N-phenyl-spiro[1H-isobenzofuran-3,3'-azetidine]-1'-carboxamide LCMS m/e 596 (M+H); 1H NMR (400 MHz, CHLOROFORM-d) δ ppm 7.77 (d, J=8.0 Hz, 1H), 7.68 (s, 1H), 7.57 (d, J=8.0 Hz, 1H), 7.43 (d, J=7.6 Hz, 2H), 7.39 (d, J=5.9 Hz, 2H), 7.31 (t, J=7.9 Hz, 2H), 7.10-7.04 (m, 1H), 6.14 (s, 1H), 5.18 (s, 2H), 4.46 (d, J=8.9 Hz, 2H), 4.30-4.19 (m, 3H), 3.89 (d, J=17.6 Hz, 1H)

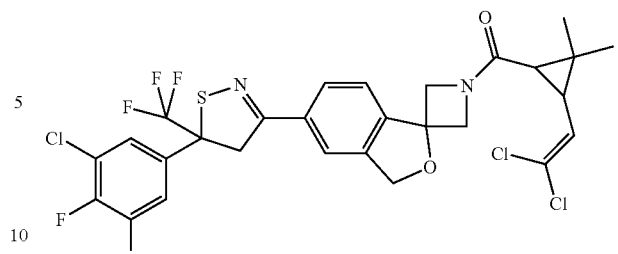

Example 24

[6-[5-(3,5-dichloro-4-fluoro-phenyl)-5-(trifluoromethyl)-4H-isothiazol-3-yl]spiro[1H-isobenzofuran-3,3'-azetidine]-1'-yl]-[3-(2,2-dichlorovinyl)-2,2-dimethyl-cyclopropyl]methanone LCMS m/e 669 (M+H); 1H NMR (400 MHz, CHLOROFORM-d) δ ppm 7.77 (d, J=7.0 Hz, 1H), 7.68 (s, 1H), 7.51 (d, J=8.2 Hz, 1H), 7.39 (d, J=5.8 Hz, 2H), 6.47 (d, J=9.3 Hz, 1H), 5.17 (s, 2H), 4.61-4.53 (m, 1H), 4.42-4.33 (m, 2H), 4.29-4.19 (m, 2H), 3.88 (d, J=17.5 Hz, 1H), 2.06-2.00 (m, 1H), 1.65-1.62 (m, 1H), 1.37-1.28 (m, 6H)

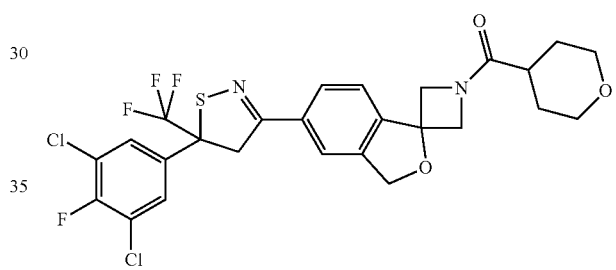

Example 25

[6-[5-(3,5-dichloro-4-fluoro-phenyl)-5-(trifluoromethyl)-4H-isothiazol-3-yl]spiro[1H-isobenzofuran-3,3'-azetidine]-1'-yl]-tetrahydropyran-4-yl-methanone LCMS m/e 589 (M+H); 1H NMR (400 MHz, CHLOROFORM-d) δ ppm 7.76 (t, J=6.5 Hz, 1H), 7.67 (d, J=5.3 Hz, 1H), 7.46 (d, J=8.0 Hz, 1H), 7.39 (d, J=5.9 Hz, 2H), 5.17 (s, 2H), 4.55 (d, J=9.0 Hz, 1H), 4.42-4.35 (m, 2H), 4.31-4.26 (m, 1H), 4.22 (d, J=17.5 Hz, 1H), 4.05 (d, J=11.6 Hz, 2H), 3.88 (d, J=17.5 Hz, 1H), 3.44 (dt, J=2.1, 11.7 Hz, 2H), 2.54-2.44 (m, 1H), 1.99-1.86 (m, 2H), 1.67 (d, J=11.8 Hz, 2H)

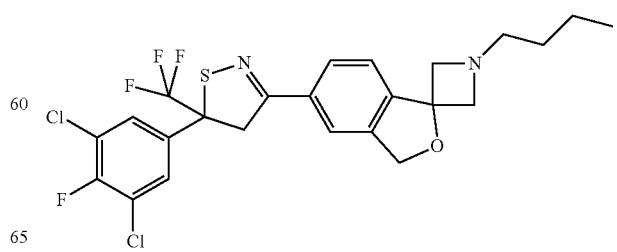

Example 26

1'-butyl-6-[5-(3,5-dichloro-4-fluoro-phenyl)-5-(trifluoromethyl)-4H-isothiazol-3-yl]spiro[1H-isobenzofuran-3,3'-azetidine]

LCMS m/e 533 (M+H); 1H NMR (400 MHz, CHLOROFORM-d) δ ppm 7.81-7.70 (m, 2H), 7.62 (s, 1H), 7.40 (d, J=5.9 Hz, 2H), 5.10 (s, 2H), 4.23 (d, J=17.5 Hz, 1H), 3.91-3.84 (m, 1H), 3.63 (d, J=6.3 Hz, 2H), 3.38 (d, J=8.3 Hz, 2H), 2.59-2.52 (m, 2H), 1.45-1.35 (m, 5H)

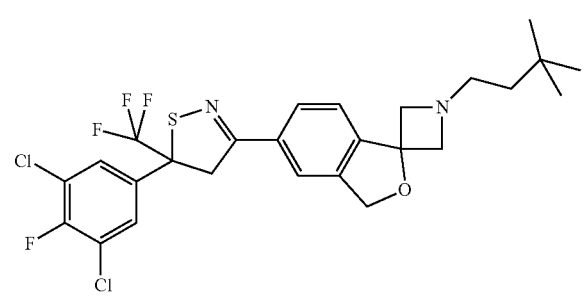 [SMILES: CC(C)(C)CCN1CC2(C1)OCc1cc(C3=NSC(c4cc(Cl)c(F)c(Cl)c4)(C(F)(F)F)C3)ccc12]

Example 27

6-[5-(3,5-dichloro-4-fluoro-phenyl)-5-(trifluoromethyl)-4H-isothiazol-3-yl]-1'-(3,3-dimethylbutyl)spiro[1H-isobenzofuran-3,3'-azetidine]

LCMS m/e 561 (M+H); 1H NMR (400 MHz, CHLOROFORM-d) δ ppm 7.79-7.69 (m, 2H), 7.62 (s, 1H), 7.40 (d, J=5.9 Hz, 2H), 5.10 (s, 2H), 4.23 (d, J=17.5 Hz, 1H), 3.88 (d, J=17.5 Hz, 1H), 3.63 (d, J=8.4 Hz, 2H), 3.38-3.34 (m, 2H), 2.59-2.53 (m, 2H), 1.35-1.30 (m, 2H), 0.94 (s, 9H)

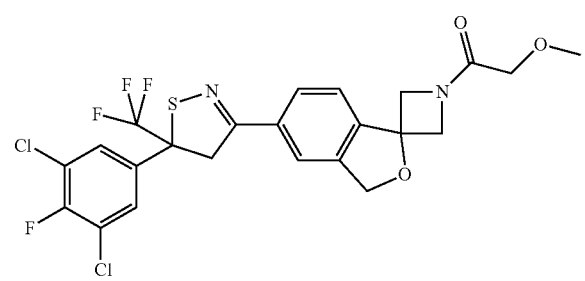 [SMILES: COCC(=O)N1CC2(C1)OCc1cc(C3=NSC(c4cc(Cl)c(F)c(Cl)c4)(C(F)(F)F)C3)ccc12]

Example 28

1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-2-methoxy-ethanone LCMS m/e 549 (M+H); 1H NMR (400 MHz, CHLOROFORM-d) δ ppm 7.76 (d, J=7.6 Hz, 1H), 7.67 (br. s., 1H), 7.50 (d, J=8.0 Hz, 1H), 7.39 (d, J=5.9 Hz, 2H), 5.16 (br. s., 2H), 4.63 (d, J=10.4 Hz, 1H), 4.53-4.42 (m, 2H), 4.34 (d, J=10.9 Hz, 1H), 4.22 (d, J=17.5 Hz, 1H), 4.08 (s, 2H), 3.88 (d, J=17.4 Hz, 1H), 3.43 (s, 3H)

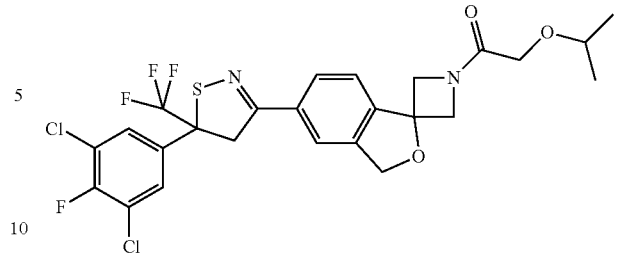

Example 29

1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-2-isopropoxy-ethanone LCMS m/e 577 (M+H); 1H NMR (400 MHz, CHLOROFORM-d) δ ppm 7.76 (dd, J=3.3, 7.7 Hz, 1H), 7.67 (d, J=4.2 Hz, 1H), 7.52 (d, J=8.0 Hz, 1H), 7.39 (d, J=5.9 Hz, 2H), 5.16 (s, 2H), 4.68 (d, J=10.5 Hz, 1H), 4.55 (d, J=10.5 Hz, 1H), 4.46-4.40 (m, 1H), 4.35-4.29 (m, 1H), 4.23 (d, J=17.5 Hz, 1H), 4.12 (s, 2H), 3.88 (d, J=17.6 Hz, 1H), 3.66 (td, J=6.1, 12.2 Hz, 1H), 1.20 (d, J=6.1 Hz, 6H)

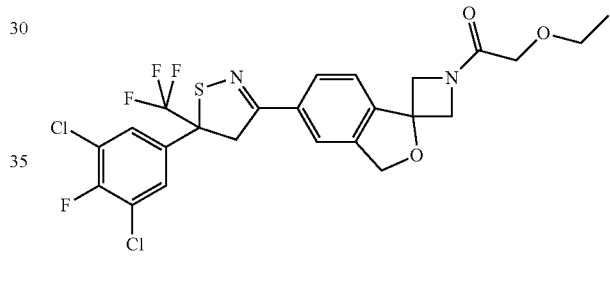

Example 30

1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-2-ethoxy-ethanone LCMS m/e 563 (M+H); 1H NMR (400 MHz, CHLOROFORM-d) δ ppm 7.79-7.74 (m, 1H), 7.69-7.66 (m, 1H), 7.51 (d, J=8.0 Hz, 1H), 7.39 (d, J=5.9 Hz, 2H), 5.17 (s, 2H), 4.68-4.64 (m, 1H), 4.55-4.51 (m, 1H), 4.46-4.41 (m, 1H), 4.35-4.30 (m, 1H), 4.23 (d, J=17.5 Hz, 1H), 4.13-4.12 (m, 2H), 3.90 (s, 1H), 3.57 (q, J=7.0 Hz, 2H), 1.24 (s, 3H)

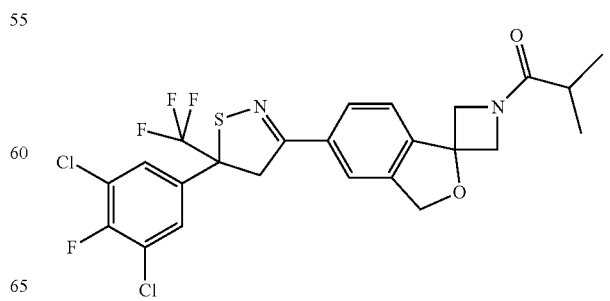

Example 31

1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-2-methyl-propan-1-one

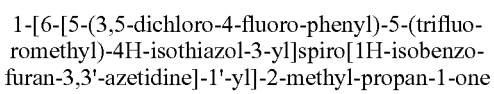

LCMS m/e 547 (M+H); 1H NMR (400 MHz, CHLOROFORM-d) δ ppm 7.79-7.73 (m, 1H), 7.67 (d, J=4.8 Hz, 1H), 7.47 (d, J=8.0 Hz, 1H), 7.39 (d, J=5.9 Hz, 2H), 5.17 (s, 2H), 4.54 (d, J=9.1 Hz, 1H), 4.41-4.32 (m, 2H), 4.30-4.19 (m, 2H), 3.88 (d, J=17.6 Hz, 1H), 2.57-2.49 (m, 1H), 1.17 (t, J=6.2 Hz, 6H)

Example 32

1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]propan-1-one

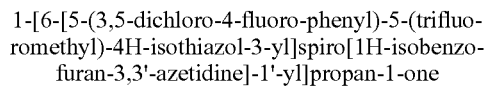

LCMS m/e 533 (M+H); 1H NMR (400 MHz, CHLOROFORM-d) δ ppm 7.80-7.73 (m, 1H), 7.67 (d, J=4.8 Hz, 1H), 7.48 (d, J=8.0 Hz, 1H), 7.39 (d, J=5.9 Hz, 2H), 5.16 (s, 2H), 4.49 (s, 1H), 4.37 (s, 1H), 4.34-4.25 (m, 2H), 4.22 (d, J=17.5 Hz, 1H), 3.88 (d, J=17.4 Hz, 1H), 2.26-2.18 (m, 2H), 1.19 (t, J=7.5 Hz, 3H)

Example 33

1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]ethanone

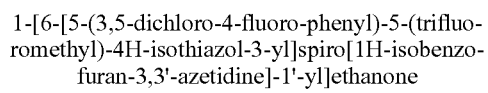

LCMS m/e 519 (M+H); 1H NMR (400 MHz, CHLOROFORM-d) δ ppm 7.76 (d, J=5.5 Hz, 1H), 7.67 (d, J=4.7 Hz, 1H), 7.50 (d, J=8.0 Hz, 1H), 7.39 (d, J=5.9 Hz, 2H), 5.17 (s, 2H), 4.52 (d, J=9.1 Hz, 1H), 4.42-4.31 (m, 2H), 4.30-4.19 (m, 2H), 3.88 (d, J=17.5 Hz, 1H), 1.98 (s, 3H)

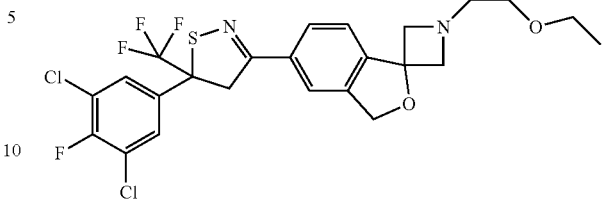

Example 34

1-[6-[5-(3,5-dichloro-4-fluoro-phenyl)-1,1-dioxo-5-(trifluoromethyl)-4H-isothiazol-3-yl]spiro[1H-isobenzofuran-3,3'-azetidine]-1'-yl]-3,3,3-trifluoropropan-1-one LCMS m/e 619 (M+H); 1H NMR (400 MHz, CHLOROFORM-d) δ ppm 8.11 (d, J=7.9 Hz, 1H), 8.01 (s, 1H), 7.66 (d, J=8.0 Hz, 1H), 7.56 (d, J=5.8 Hz, 2H), 5.26 (s, 2H), 4.66 (d, J=9.6 Hz, 1H), 4.54-4.44 (m, 2H), 4.38 (d, J=11.0 Hz, 1H), 4.26 (d, J=17.8 Hz, 1H), 4.03 (d, J=17.8 Hz, 1H), 3.17-3.03 (m, 2H)

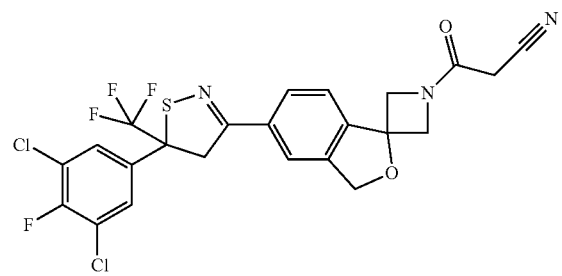 [SMILES: N#CCC(=O)N1CC2(C1)OCc1cc(C3=NSC(c4cc(Cl)c(F)c(Cl)c4)(C(F)(F)F)C3)ccc12]

Example 35

3-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-3-oxo-propanenitrile LCMS m/e 544 (M+H); 1H NMR (400 MHz, CHLOROFORM-d) δ ppm 7.80-7.76 (m, 1H), 7.71-7.68 (m, 1H), 7.54-7.50 (m, 1H), 7.39 (d, J=5.9 Hz, 2H), 5.18 (s, 2H), 4.69-4.64 (m, 1H), 4.56-4.45 (m, 2H), 4.39-4.34 (m, 1H), 4.26-4.20 (m, 1H), 3.91-3.85 (m, 1H), 3.37 (s, 2H)

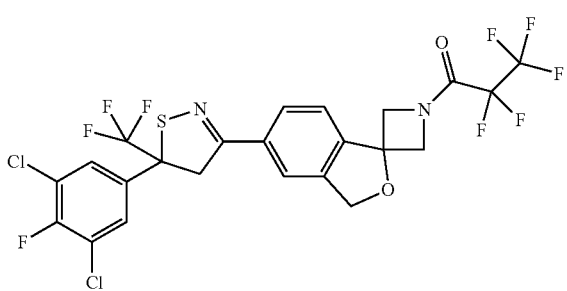 [SMILES: O=C(N1CC2(C1)OCc1cc(C3=NSC(c4cc(Cl)c(F)c(Cl)c4)(C(F)(F)F)C3)ccc12)C(F)(F)C(F)(F)F]

Example 36

1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-2,2,3,3,3-pentafluoro-propan-1-one LCMS m/e 575 (M+H); 1H NMR (400 MHz, CHLOROFORM-d) δ ppm 7.83 (d, J=8.0 Hz, 1H), 7.76-7.72 (m, 2H), 7.39 (d, J=5.9 Hz, 2H), 5.15 (s, 2H), 4.76 (d, J=9.4 Hz, 2H), 4.62 (d, J=10.2 Hz, 2H), 4.23 (d, J=17.6 Hz, 1H), 3.88 (d, J=17.7 Hz, 1H)

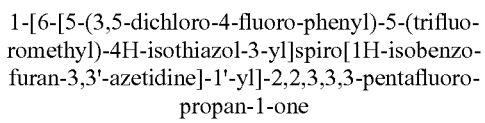

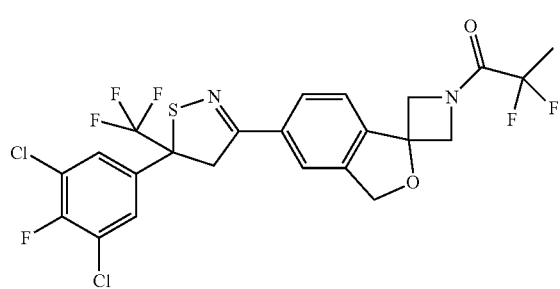 [SMILES: CC(F)(F)C(=O)N1CC2(C1)OCc1cc(C3=NSC(c4cc(Cl)c(F)c(Cl)c4)(C(F)(F)F)C3)ccc12]

Example 37

1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-2,2-difluoro-propan-1-one LCMS m/e 567 (M+H); 1H NMR (400 MHz, CHLOROFORM-d) δ ppm 7.77 (d, J=7.9 Hz, 1H), 7.69-7.65 (m, 1H), 7.51 (d, J=8.0 Hz, 1H), 7.39 (d, J=5.8 Hz, 2H), 5.20-5.14 (m, 2H), 4.77 (d, J=11.6 Hz, 1H), 4.64 (d, J=9.0 Hz, 1H), 4.51-4.46 (m, 1H), 4.39-4.34 (m, 1H), 4.23 (d, J=17.5 Hz, 1H), 3.88 (d, J=17.5 Hz, 1H), 2.81 (s, 3H)

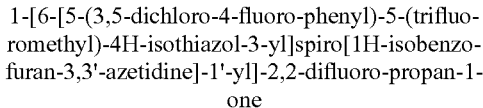

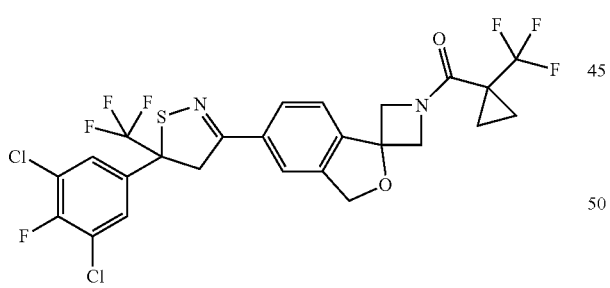

Example 38

[6-[5-(3,5-dichloro-4-fluoro-phenyl)-5-(trifluoromethyl)-4H-isothiazol-3-yl]spiro[1H-isobenzofuran-3,3'-azetidine]-1'-yl]-[1-(trifluoromethyl)cyclopropyl] methanone LCMS m/e 613 (M+H); 1H NMR (400 MHz, CHLOROFORM-d) δ ppm 7.77 (d, J=8.0 Hz, 1H), 7.70-7.67 (m, 1H), 7.46 (d, J=8.0 Hz, 1H), 7.39 (d, J=5.9 Hz, 2H), 5.17 (s, 2H), 4.75-4.27 (m, 4H), 4.23 (d, J=17.5 Hz, 1H), 3.88 (d, J=17.5 Hz, 1H), 0.91-0.83 (m, 4H)

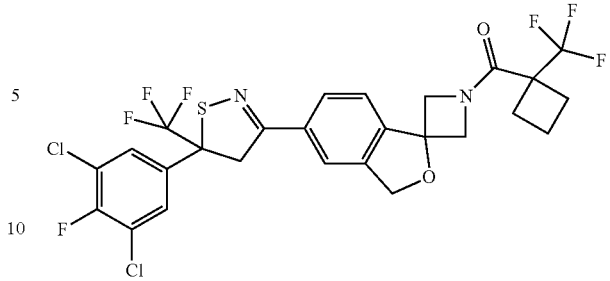

Example 39

[6-[5-(3,5-dichloro-4-fluoro-phenyl)-5-(trifluoromethyl)-4H-isothiazol-3-yl]spiro[1H-isobenzofuran-3,3'-azetidine]-1'-yl]-[1-(trifluoromethyl)cyclobutyl] methanone LCMS m/e 627 (M+H); 1H NMR (400 MHz, CHLOROFORM-d) δ ppm 7.75 (d, J=7.6 Hz, 1H), 7.67 (br. s., 1H), 7.45 (d, J=8.0 Hz, 1H), 7.39 (d, J=5.9 Hz, 2H), 5.16 (d, J=3.9 Hz, 2H), 4.58 (d, J=9.3 Hz, 1H), 4.50-4.44 (m, 1H), 4.42-4.33 (m, 2H), 4.22 (d, J=17.5 Hz, 1H), 3.87 (d, J=17.3 Hz, 1H), 2.78-2.58 (m, 2H), 2.56-2.38 (m, 2H), 2.22-2.07 (m, 1H), 1.97-1.85 (m, 1H)

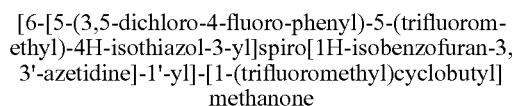

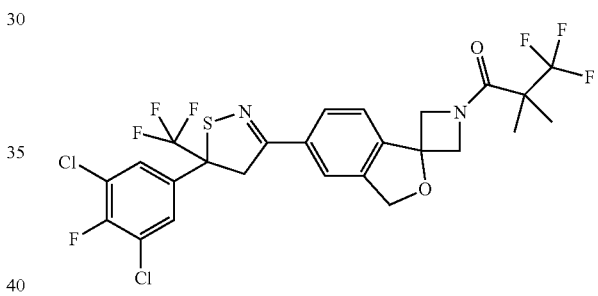

Example 40

1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-3,3,3-trifluoro-2,2-dimethyl-propan-1-one LCMS m/e 615 (M+H); 1H NMR (400 MHz, CHLOROFORM-d) δ ppm 7.76 (d, J=7.8 Hz, 1H), 7.67 (s, 1H), 7.45 (d, J=8.0 Hz, 1H), 7.39 (d, J=5.9 Hz, 2H), 5.31 (s, 2H), 5.16 (s, 2H), 4.22 (d, J=17.5 Hz, 1H), 3.88 (d, J=17.5 Hz, 1H), 3.50 (s, 2H), 1.48 (s, 6H)

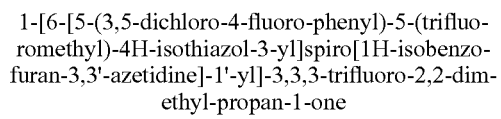

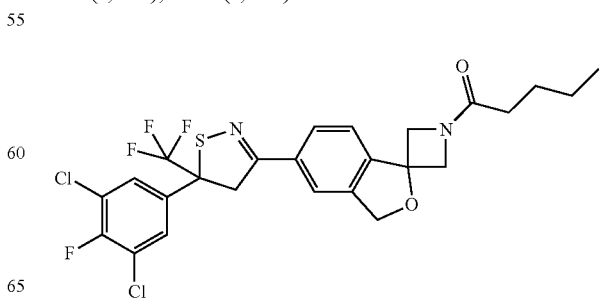

Example 41

1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]pentan-1-one LCMS m/e 561 (M+H); 1H NMR (400 MHz, CHLOROFORM-d) δ ppm 7.79-7.72 (m, 1H), 7.70-7.65 (m, 1H), 7.49 (s, 1H), 7.39 (d, J=5.9 Hz, 2H), 5.16 (s, 2H), 4.53-4.48 (m, 1H), 4.41-4.36 (m, 1H), 4.33-4.30 (m, 1H), 4.29-4.25 (m, 1H), 4.22 (d, J=17.5 Hz, 1H), 3.91-3.85 (m, 1H), 2.22-2.16 (m, 2H), 1.72-1.60 (m, 2H), 1.39 (d, J=7.4 Hz, 2H), 0.97-0.92 (m, 3H)

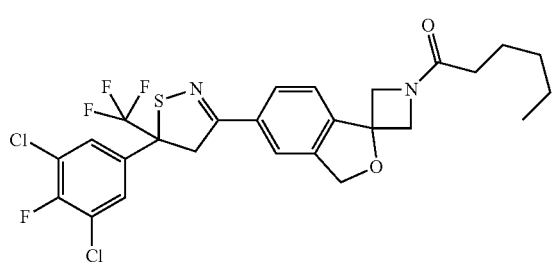 [SMILES: CCCCCC(=O)N1CC2(C1)OCc1cc(C3=NSC(c4cc(Cl)c(F)c(Cl)c4)(C(F)(F)F)C3)ccc12]

Example 42

1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]hexan-1-one LCMS m/e 575 (M+H); 1H NMR (400 MHz, CHLOROFORM-d) δ ppm 7.79-7.73 (m, 1H), 7.67 (d, J=5.6 Hz, 1H), 7.48 (d, J=8.0 Hz, 1H), 7.39 (d, J=5.9 Hz, 2H), 5.16 (s, 2H), 4.49 (s, 1H), 4.37 (s, 1H), 4.31 (d, J=17.4 Hz, 2H), 4.22 (d, J=17.5 Hz, 1H), 3.88 (d, J=17.5 Hz, 1H), 2.37-2.32 (m, 1H), 2.18 (t, J=7.6 Hz, 2H), 1.37-1.33 (m, 4H), 0.94-0.88 (m, 4H)

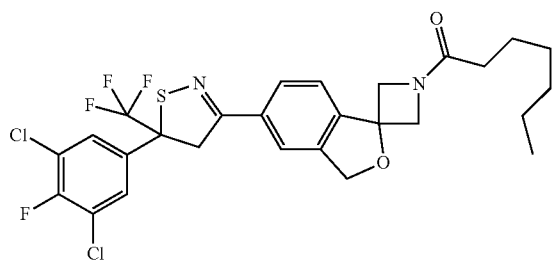 [SMILES: CCCCCCC(=O)N1CC2(C1)OCc1cc(C3=NSC(c4cc(Cl)c(F)c(Cl)c4)(C(F)(F)F)C3)ccc12]

Example 43

1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]heptan-1-one LCMS m/e 589 (M+H); 1H NMR (400 MHz, CHLOROFORM-d) δ ppm 7.79-7.73 (m, 1H), 7.69-7.65 (m, 1H), 7.50-7.46 (m, 1H), 7.39 (d, J=5.9 Hz, 2H), 5.17 (s, 2H), 4.53-4.48 (m, 1H), 4.41-4.35 (m, 1H), 4.34-4.25 (m, 2H), 4.25-4.19 (m, 1H), 3.92-3.83 (m, 1H), 2.19 (s, 2H), 1.72-1.65 (m, 2H), 1.35-1.31 (m, 6H), 0.84 (d, J=2.2 Hz, 3H)

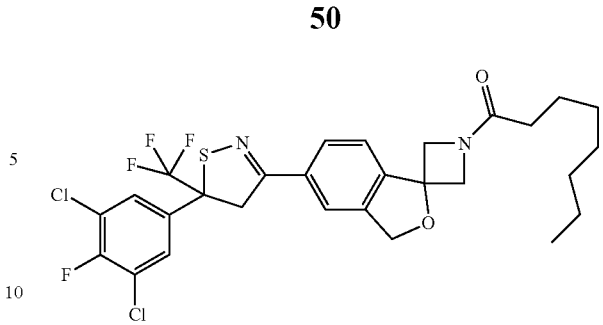

Example 44

1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]octan-1-one LCMS m/e 603 (M+H); 1H NMR (400 MHz, CHLOROFORM-d) δ ppm 7.79-7.73 (m, 1H), 7.69-7.65 (m, 1H), 7.48 (d, J=8.0 Hz, 1H), 7.39 (d, J=5.9 Hz, 2H), 5.16 (s, 2H), 4.53-4.48 (m, 1H), 4.37 (s, 1H), 4.28 (s, 2H), 4.22 (d, J=17.5 Hz, 1H), 3.90 (s, 1H), 2.18 (t, J=7.6 Hz, 2H), 1.68 (br. s., 2H), 1.35-1.29 (m, 9H), 0.91-0.88 (m, 9H)

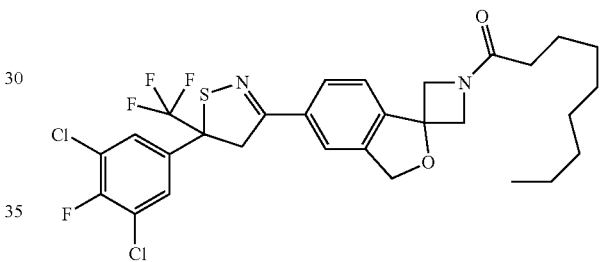

Example 45

1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]nonan-1-one LCMS m/e 617 (M+H); 1H NMR (400 MHz, CHLOROFORM-d) δ ppm 7.79-7.73 (m, 1H), 7.67 (d, J=5.7 Hz, 1H), 7.48 (d, J=8.0 Hz, 1H), 7.39 (d, J=5.9 Hz, 2H), 5.17 (s, 2H), 4.51 (d, J=9.1 Hz, 1H), 4.41-4.36 (m, 1H), 4.29 (dd, J=10.0, 17.8 Hz, 2H), 4.22 (d, J=17.5 Hz, 1H), 3.88 (d, J=17.5 Hz, 1H), 2.18 (t, J=7.6 Hz, 2H), 1.70-1.65 (m, 2H), 1.32 (d, J=7.5 Hz, 9H), 0.90-0.86 (m, 13H)

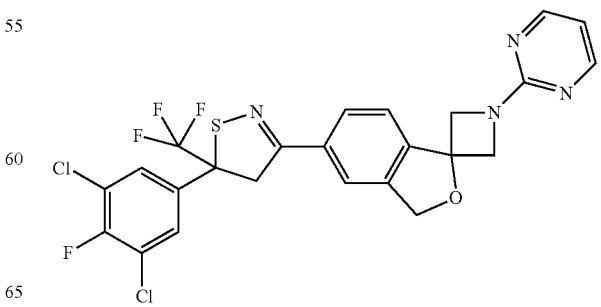

Example 46

6-[5-(3,5-dichloro-4-fluoro-phenyl)-5-(trifluoromethyl)-4H-isothiazol-3-yl]-1'-pyrimidin-2-yl-spiro [1H-isobenzofuran-3,3'-azetidine]

1H NMR (400 MHz, CHLOROFORM-d) δ ppm 8.39 (d, J=4.8 Hz, 2H), 7.75 (d, J=8.0 Hz, 1H), 7.69 (s, 1H), 7.58 (d, J=8.0 Hz, 1H), 7.39 (d, J=5.9 Hz, 2H), 6.64 (t, J=4.8 Hz, 1H), 5.21 (s, 2H), 4.53 (d, J=10.0 Hz, 2H), 4.39 (d, J=9.6 Hz, 2H), 4.23 (d, J=17.5 Hz, 1H), 3.89 (d, J=17.6 Hz, 1H)

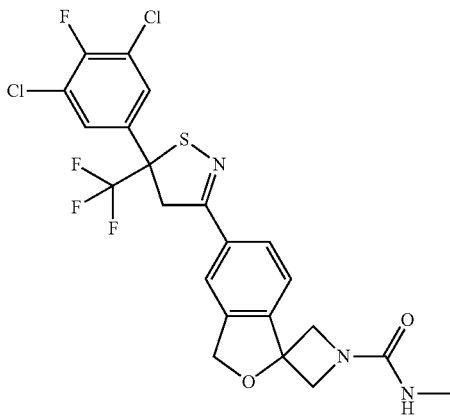 [SMILES: CNC(=O)N1CC2(C1)OCc1cc(C3=NSC(c4cc(Cl)c(F)c(Cl)c4)(C(F)(F)F)C3)ccc12]

Example 47

6-[5-(3,5-dichloro-4-fluoro-phenyl)-5-(trifluoromethyl)-4H-isothiazol-3-yl]-N-methyl-spiro[1H-isobenzofuran-3,3'-azetidine]-1'-carboxamide LCMS m/e 534 (M+H); 1H NMR (400 MHz, CHLOROFORM-d) δ ppm 7.79-7.72 (m, 1H), 7.66 (s, 1H), 7.54 (d, J=8.0 Hz, 1H), 7.39 (d, J=5.9 Hz, 2H), 5.15 (s, 2H), 4.34 (d, J=8.8 Hz, 2H), 4.22 (d, J=17.5 Hz, 1H), 4.16-4.13 (m, 2H), 3.88 (d, J=17.6 Hz, 1H), 2.86 (d, J=4.8 Hz, 3H)

Evaluation

The biological activity of compounds of the present invention was tested using the test methods described below.

*R. sanguineus, D. variablis, A. americanum*, and *I. scapularis* Residual Adult Contact Assay A solution of the test compounds was used to coat the inner wall of glass vials and to treat two filter papers. Once dried, one filter paper was placed in the cap of the vial and the other in the bottom of the vial. Each treated vial was infested with 10 ticks. Contact of the ticks with residues was induced by holding the vials in a controlled environment and assessment was performed at 12, 24 and 48 hours after application in comparison with untreated glass vials and solvent-treated glass vials. Compounds were tested in duplicate and two separate trials (n=4).

Preferred compounds of the invention are generally active at below 500 ppm at 48 hours in the assay.

Compound reference numbers 1, 2, 4-10, 14-16, 19, 22-27, 29, 31, 32, 34-38, and 41 were active at below 50 ppm at 48 hours in this assay and, as such, are especially preferred for such intended use.

*Ctenocephalides felis* Residual Contact Assay

A solution of the test compounds, individually and in combination was dispensed onto a substrate placed into a glass vial. The treated surface was allowed to dry before infesting each vial with 10 adult *Ctenocephalides felis*. The treated vials were held in a controlled environment and assessment was performed at 6, 24 and 48 hours after application in comparison with untreated controls glass vials and solvent-treated glass vials. Compounds were tested in duplicate and two separate trials (n=4).

Preferred compounds of the invention are generally active at below 500 ppm at 48 hours in the assay.

Compound reference numbers 1, 2, 4, and 5 were active at below 50 ppm at 48 hours in this assay and, as such, are especially preferred for such intended use.

In Vitro Evaluation of Ingestion Activity Against Fleas (*Ctenocephalides Felis*)

For flea ingestion tests, an aliquot of each compound stock was added to organic bovine blood contained in an artificial feeding container, with a final DMSO concentration of 0.5%. Ten newly emerged unfed fleas, *Ctenocephalides felis*, from a laboratory colony, 0-7 days old, were aspirated into a chamber and exposed to the appropriate feeding container and held in a controlled environment at 35° C. Fleas were evaluated for % mortality at 24, 48, and 72 hours post infestation. Fleas showing normal movement and/or jumping ability were considered viable and those showing no movement after tapping the vials were scored as dead. The compound+blood mixture was replaced every 24 hours.

Preferred compounds of the invention are generally active at below 500 ppm at 24 hours in this assay.

Compound reference numbers 1, 2, 4-10, 14-17, 19, 20, 22-27, 29-38, and 41 were active at below 50 ppm at 48 hours in this assay and, as such, are especially preferred for such intended use.

*Dirofilaria immitis* Microfilariae Motility Assay

*Dirofilaria immitis* microfilariae are isolated by filtration from blood of an infected beagle dog allowed to incubate at 37C/5% $CO_2$/95% RH in RPMI media. For assay 500 microfilariae are added into 96-well plates followed by addition of compounds diluted in DMSO for single-point or dose response (5-point) analysis. Ivermectin or emodepside are included as a positive control and DMSO-only wells are included as negative controls. Plates containing parasites and compounds are incubated at 37° C./5% $CO_2$/95% RH for 72 hours and motility is assessed using an LCD camera imaging system. Percent motility inhibition values are generated relative to the average of the DMSO-only wells. For dose response analysis, data points were averaged and curve fitting software is used to generate sigmoidal curves for the determination of $EC_{50}$ values (i.e. the effective concentration to kill 50% of the organism).

Preferred compounds of the invention are generally active at below 100 μM in this assay.

Particularly preferred compounds are active below 10 μM, such as compounds 1, 13, 16-17, 19-27, 29-31, 35, 36, 40, and 41, and therefore are preferred for such use.

In Vitro Evaluation of Ingestion Activity Against Mosquitoes (*Aedes aegypti*)

A solution of test compounds is added to bovine blood contained in a feeding chamber to reach the desired final concentration. Blood spiked with DMSO is prepared to serve as control. Adult female mosquitoes are introduced at the bottom of the chamber and allowed to feed on blood mixtures containing DMSO or test compounds for 30 minutes. Fully engorged mosquitoes are sorted into clean chambers after the blood meal and monitored for survival over 3 days. Replicates containing 10 mosquitoes are performed with each test compound concentration and results calculated as % mortality at specific time points.

Preferred compounds of the invention are generally active at below 500 ppm at 20 hours in this assay.

Compound reference numbers 1, 6-8, 10, 12, 16, 17, 19, 20, 22-27, 29, 30, 35, and 41 were active at below 1 ppm at 20 hours in this assay and are especially preferred for such intended use.

In Vitro Evaluation of Contact Activity Against Mosquitoes (*Aedes aegypti*)

A solution of the test compound is used to coat the inner walls of glass vials and allowed to dry overnight. Five female *Aedes aegypti* adults are added to each vial. Contact of the mosquitoes is induced by holding the vials in a controlled environment and assessment of mortality/knockdown is performed at 24 hours after application in comparison to solvent-treated glass vials. Compounds are tested in duplicate on a total of 10 mosquitoes/treatment dose.

Preferred compounds of the invention are generally active at below 500 ppm at 48 hours in the assay.

In Vitro Evaluation of Contact Activity Against Flies (*Stomoxys calcitrans*)

A solution of the test compounds is added to a piece of filter paper embedded in a petri dish and allowed to dry overnight. Ten 2-3 day old adult flies are added to each petri dish and a sucrose-soaked dental wick is added as a food source. Flies are held at room temperature and assessed for mortality/knockdown at desired time points.

Preferred compounds of the invention are generally active at below 500 ppm at 48 hours in the assay.

In Vitro Flea Activity—Comparison with Fluralaner, Afoxolaner, and (+/−)Sarolaner Using known and described methods, Compound Reference Number 1 was compared to fluralaner, afoxolaner, and (+/−)sarolaner in contact and ingestion assays. Fluralaner is sold under the tradename Bravecto® by Merck Animal Health. Afoxolaner is sold under the tradename Nexgard® by Merial Ltd. Sarolaner is sold under the tradename Simparica® by Zoetis, Inc. As noted herein, for the comparison studies racemic sarolaner "(+/−)" was used.

The results are provided:

| Compound | Ingestion EC50 | | Contact EC50 |
|---|---|---|---|
| | 2 h, ppm | 24 h, ppm | 48 h, ppm |
| Compound Ref. No. 1 | 2.6 ± 0.3 | 0.20 ± 0.10 | 29.0 ± 0.3 |
| Fluralaner | 1.6 ± 0.7 | 0.06 ± 0.02 | >50 |
| Afoxolaner | 6.0 ± 2.9 | 0.13 ± 0.05 | >50 |
| (+/−) Sarolaner | NT | 1.23 ± 0.11 | NT |

The compounds of the present invention, as represented by compound reference number 1, provide comparable potency by ingestion and superior potency by contact to commercially available standards of treatment.

In Vitro Tick Activity—Comparison with Fluralaner, Afoxolaner, and (+/−)Sarolaner Using known and described methods, Compound Reference Number 1 was compared to fluralaner, afoxolaner, and (+/−)sarolaner in contact assays on several tick species. The results are provided:

| Compound | *R. sanguineus* Contact $EC_{50}$ 24 h, ppm | *D. variabilis* Contact $EC_{50}$ 24 h, ppm | *A. americanum* Contact $EC_{50}$ 24 h, ppm | *I. scapularis* Contact $EC_{50}$ 24 h, ppm |
|---|---|---|---|---|
| Comp. Ref. No. 1 | 17.0 ± 3.8 | 12.2 ± 0.6 | 13.5 ± 5.1 | 2.0 ± 0.4 |
| fluralaner | 37.1 ± 16.3 | 18.4 ± 3.0 | 12.4, >50 | 6.4 ± 3.3 |
| afoxolaner | >50 | >50 | 31.6, >50 | 17.8 ± 5.9 |
| (+/−) sarolaner | 37.8 ± 12.2 | | | |

| Compound | *R. sanguineus* Contact $EC_{50}$ 48 h, ppm | *D. variabilis* Contact $EC_{50}$ 48 h, ppm | *A. americanum* Contact $EC_{50}$ 48 h, ppm | *I. scapularis* Contact $EC_{50}$ 48 h, ppm |
|---|---|---|---|---|
| Comp. Ref. No. 1 | 4.6 ± 3.0 | 5.0 ± 1.6 | 2.7 ± 0.4 | 0.04 ± 0.02 |
| fluralaner | 9.8 ± 5.0 | 4.9 ± 1.4 | 20.4 ± 10.7 | 1.3 ± 0.2 |
| afoxolaner | 20.2 ± 5.0 | 12.35 ± 0.5 | 11.3 ± 2.3 | 5.31 ± 1.8 |
| (+/−) sarolaner | 12.7 ± 0.1 | | | |

The compounds of the present invention, as represented by compound reference number 1, provide superior potency by contact to commercially available standards of treatment.

All publications, patents and patent applications cited in this specification are incorporated herein by reference for the teaching to which such citation is used.

Test compounds for the experiments described herein were employed in free or salt form.

The specific responses observed may vary according to and depending on the particular active compound selected or whether there are present carriers, as well as the type of formulation and mode of administration employed, and such expected variations or differences in the results are contemplated in accordance with practice of the present invention.

Although specific embodiments of the present invention are herein illustrated and described in detail, the invention is not limited thereto. The above detailed descriptions are provided as exemplary of the present invention and should not be construed as constituting any limitation of the invention. Modifications will be obvious to those skilled in the art, and all modifications that do not depart from the spirit of the invention are intended to be included with the scope of the appended claims.

The invention claimed is:

1. A compound 1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-3,3,3-trifluoro-propan-1-one or a pesticidal, veterinary, or pharmaceutically acceptable salt thereof.

2. A composition comprising 1-[6-[5-(3,5-dichloro-4-fluoro-phenyl)-5-(trifluoromethyl)-4H-isothiazol-3-yl]spiro[1H-isobenzofuran-3,3'-azetidine]-1'-yl]-3,3,3-trifluoro-propan-1-one or a pesticidal, veterinary, or pharmaceutically acceptable salt thereof and one or more pesticidal, veterinary, or pharmaceutically acceptable carrier.

* * * * *